(12) United States Patent
Schriver et al.

(10) Patent No.: US 10,029,220 B2
(45) Date of Patent: *Jul. 24, 2018

(54) FLUID PATH SET WITH TURBULENT MIXING CHAMBER, BACK FLOW COMPENSATOR

(71) Applicant: BAYER HEALTHCARE LLC, Whippany, NJ (US)

(72) Inventors: Ralph H. Schriver, Tarentum, PA (US); Andreas Maihoefer, Cheswick, PA (US); James A. Dedig, Pittsburgh, PA (US); Michael A. Spohn, Fenelton, PA (US); Herbert M. Grubic, Pittsburgh, PA (US); Michael J. Swantner, Saxonburg, PA (US); Adam Caruso, Harrison City, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/417,945

(22) Filed: Jan. 27, 2017

(65) Prior Publication Data

US 2017/0136424 A1    May 18, 2017

Related U.S. Application Data

(62) Division of application No. 13/799,426, filed on Mar. 13, 2013, now Pat. No. 9,555,379.

(51) Int. Cl.
*B01F 5/06* (2006.01)
*B01F 15/00* (2006.01)
(Continued)

(52) U.S. Cl.
CPC ............. *B01F 5/061* (2013.01); *A61M 5/007* (2013.01); *A61M 5/16827* (2013.01);
(Continued)

(58) Field of Classification Search
CPC ...................................................... B01F 5/0602
(Continued)

(56) References Cited

U.S. PATENT DOCUMENTS 508,584 A    11/1893 Stevens
945,143 A    1/1910 Jacques
(Continued)

FOREIGN PATENT DOCUMENTS

JP    H0999034 A    4/1997
WO    2011011346 A1    1/2011
(Continued)

OTHER PUBLICATIONS

Patent Abstract of Japan publication No. 200804959, copyright Japanese Patent Office, 2008.*
(Continued)

*Primary Examiner* — David Sorkin
(74) *Attorney, Agent, or Firm* — Joseph L. Kent; David Schramm; James R. Stevenson

(57) ABSTRACT

A fluid path set includes a first fluid line having a proximal end fluidly connectable to a source of a first fluid and a second fluid line having a proximal end fluidly connectable to a source of a second fluid. A flow mixing device is in fluid communication with distal ends of the first and second fluid lines. The flow mixing device includes a housing, a first fluid port provided for receiving the first fluid, and a second fluid port for receiving the second fluid. A mixing chamber is disposed within the housing and is in fluid communication with the first and second fluid ports. A third fluid port in fluid communication with the mixing chamber for discharging a mixed solution of the first and second fluids. A turbulent flow inducing member is disposed within the mixing chamber for promoting turbulent mixing of the first and second fluids.

18 Claims, 34 Drawing Sheets

(51) Int. Cl.
   *B01F 3/08*    (2006.01)
   *A61M 5/00*    (2006.01)
   *A61M 5/168*   (2006.01)
   *A61M 39/10*   (2006.01)
   *B01F 5/00*    (2006.01)
   *A61M 39/00*   (2006.01)

(52) U.S. Cl.
   CPC ......... *A61M 39/105* (2013.01); *B01F 3/0861* (2013.01); *B01F 5/0645* (2013.01); *B01F 5/0651* (2013.01); *B01F 5/0696* (2013.01); *B01F 15/00831* (2013.01); *A61M 2039/0027* (2013.01); *B01F 2005/0025* (2013.01); *B01F 2005/0091* (2013.01); *B01F 2005/0622* (2013.01); *B01F 2005/0636* (2013.01); *B01F 2215/0034* (2013.01); *B01F 2215/0459* (2013.01); *B01F 2215/0468* (2013.01)

(58) Field of Classification Search
   USPC .......................... 366/163.2, 181.5, 336–340
   See application file for complete search history.

(56) References Cited

U.S. PATENT DOCUMENTS

| | | |
|---|---|---|
| 2,511,291 A | 6/1950 | Mueller |
| 2,583,206 A | 1/1952 | Borck et al. |
| 3,159,312 A | 12/1964 | Van Sciver, II |
| 3,276,472 A | 10/1966 | Jinkens et al. |
| 3,635,444 A | 1/1972 | Potter |
| 3,671,208 A | 6/1972 | Wayne |
| 3,719,207 A | 3/1973 | Takeda |
| 3,868,967 A | 3/1975 | Harding |
| 4,204,775 A | 5/1980 | Speer |
| 4,208,136 A | 6/1980 | King |
| 4,329,067 A | 5/1982 | Goudy, Jr. |
| 4,952,068 A | 8/1990 | Flint |
| 5,725,500 A | 3/1998 | Micheler |
| 6,132,396 A | 10/2000 | Antanavich et al. |
| 6,442,418 B1 | 8/2002 | Evans, III et al. |
| 6,575,930 B1 | 6/2003 | Trombley, III et al. |
| 6,731,971 B2 | 5/2004 | Evans et al. |
| 7,094,216 B2 | 8/2006 | Trombley et al. |
| 7,351,221 B2 | 4/2008 | Trombley, III |
| 7,427,281 B2 | 9/2008 | Uber et al. |
| 7,556,619 B2 | 7/2009 | Spohn et al. |
| 7,766,883 B2 | 8/2010 | Reilly et al. |
| 7,861,893 B2 | 1/2011 | Voegele et al. |
| 8,147,464 B2 | 4/2012 | Spohn et al. |
| 8,162,903 B2 | 4/2012 | Reilly et al. |
| 8,337,456 B2 | 12/2012 | Schriver et al. |
| 8,439,863 B2 | 5/2013 | Fago et al. |
| 9,555,379 B2 * | 1/2017 | Schriver ............... A61M 5/007 |
| 2004/0064041 A1 | 4/2004 | Lazzaro et al. |
| 2004/0092905 A1 | 5/2004 | Azzolini |
| 2004/0154788 A1 | 8/2004 | Symonds |
| 2005/0113754 A1 | 5/2005 | Cowan et al. |
| 2006/0052794 A1 * | 3/2006 | McGill ............... A61B 17/8816 606/93 |
| 2007/0068964 A1 | 3/2007 | Tanaami et al. |
| 2008/0086087 A1 | 4/2008 | Spohn et al. |
| 2011/0275988 A1 | 11/2011 | Davis et al. |
| 2012/0101472 A1 | 4/2012 | Schroeder et al. |
| 2012/0123257 A1 | 5/2012 | Stokes, Jr. et al. |
| 2012/0178629 A1 | 7/2012 | Hudson et al. |

FOREIGN PATENT DOCUMENTS

| | | |
|---|---|---|
| WO | 2011125303 A1 | 10/2011 |
| WO | 2012155035 A1 | 11/2012 |

OTHER PUBLICATIONS

The International Preliminary Report on Patentability and Written Opinion dated Sep. 24, 2015 from corresponding PCT Application No. PCT/US2014/026324.

The International Search Report and Written Opinion dated Jul. 18, 2014 from corresponding PCT Application No. PCT/US2014/026324, which was filed on Mar. 13, 2014.

* cited by examiner

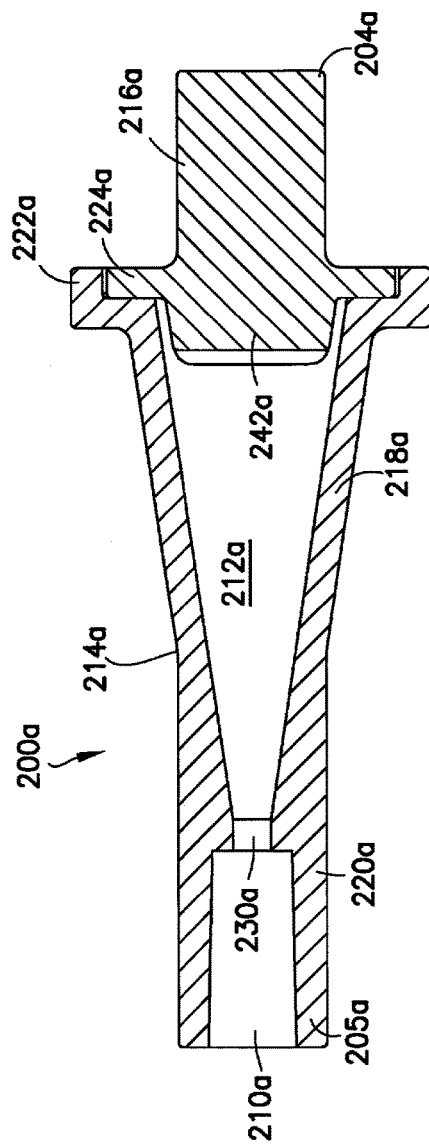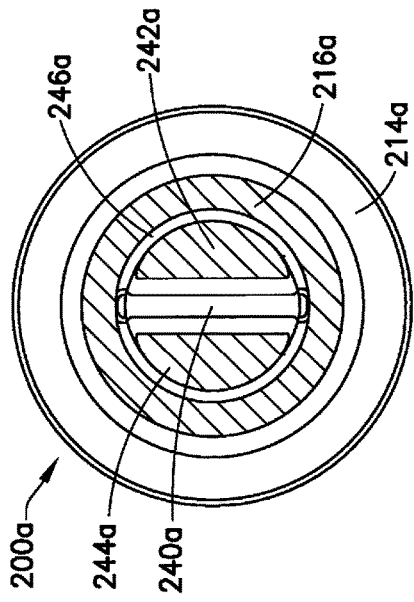

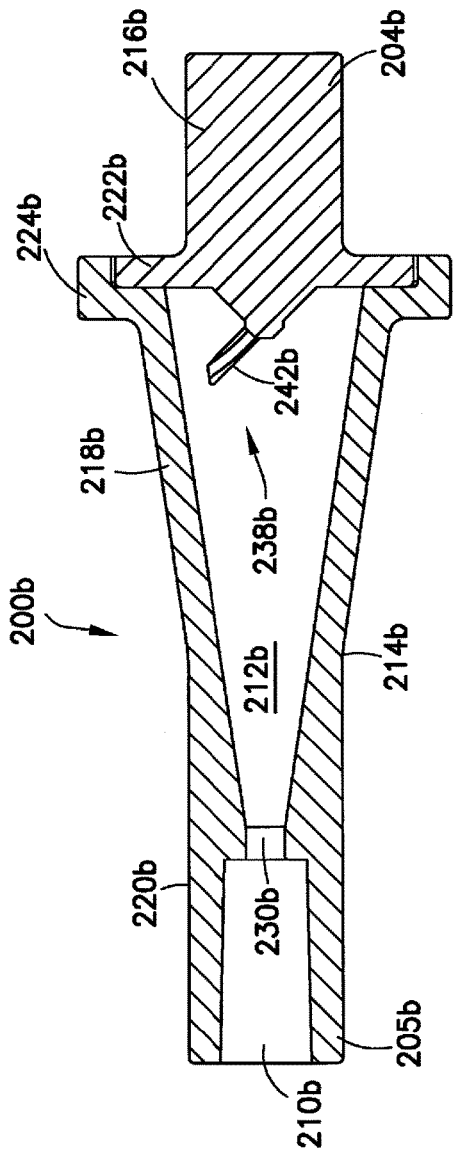
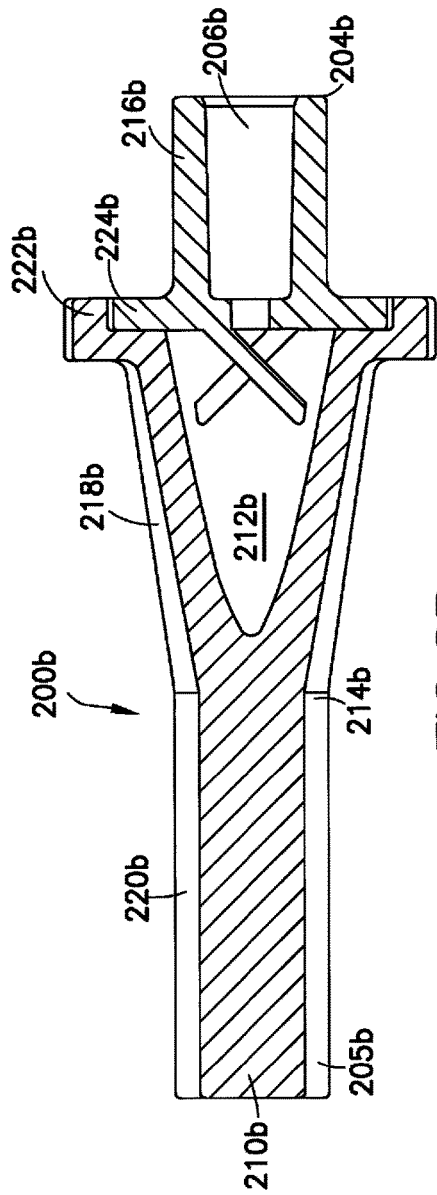
FIG. 8A
FIG. 8B

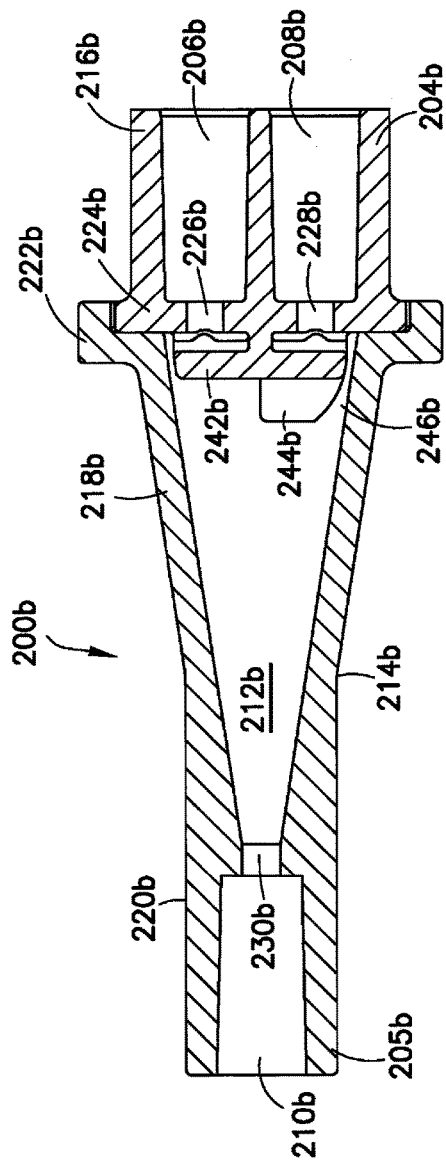
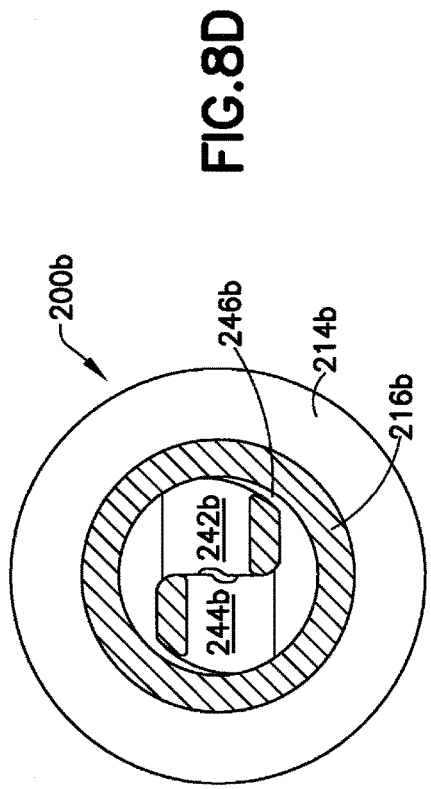

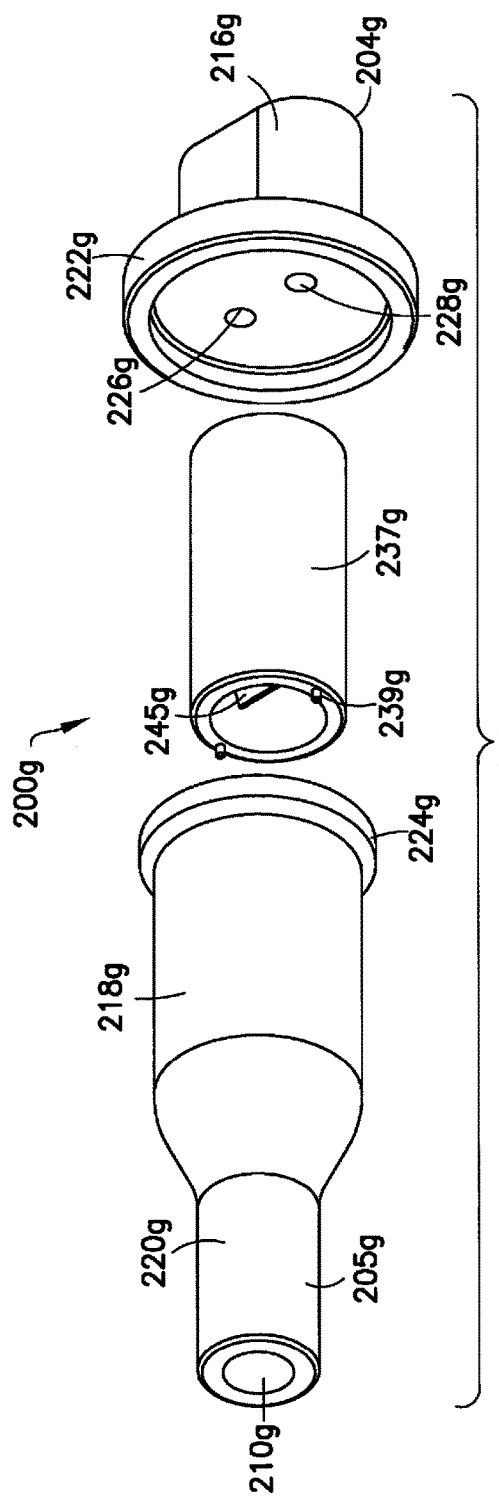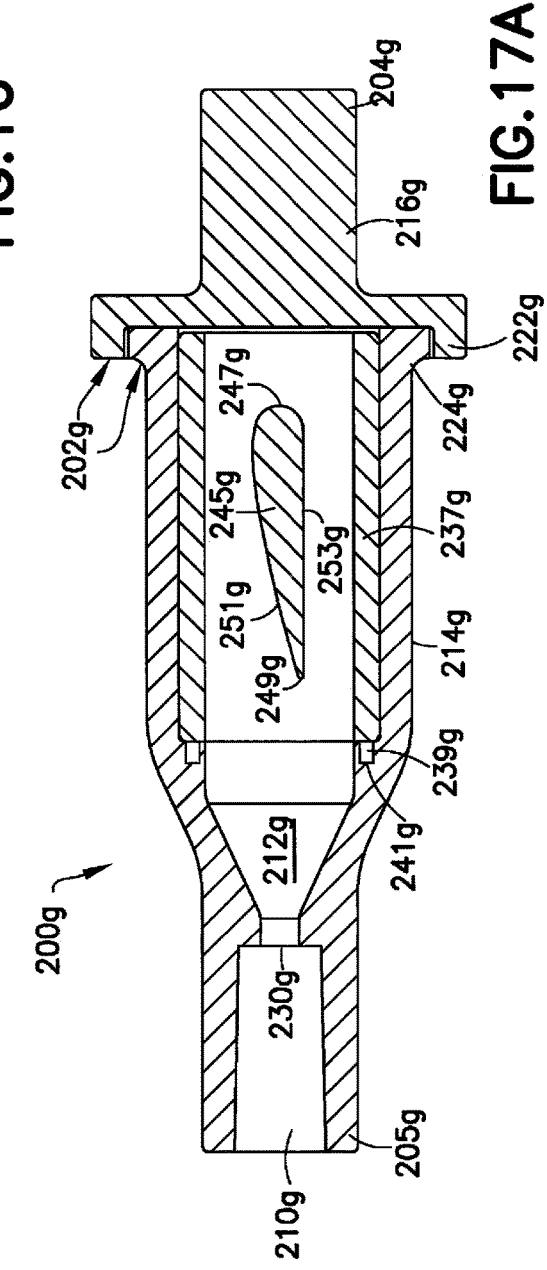

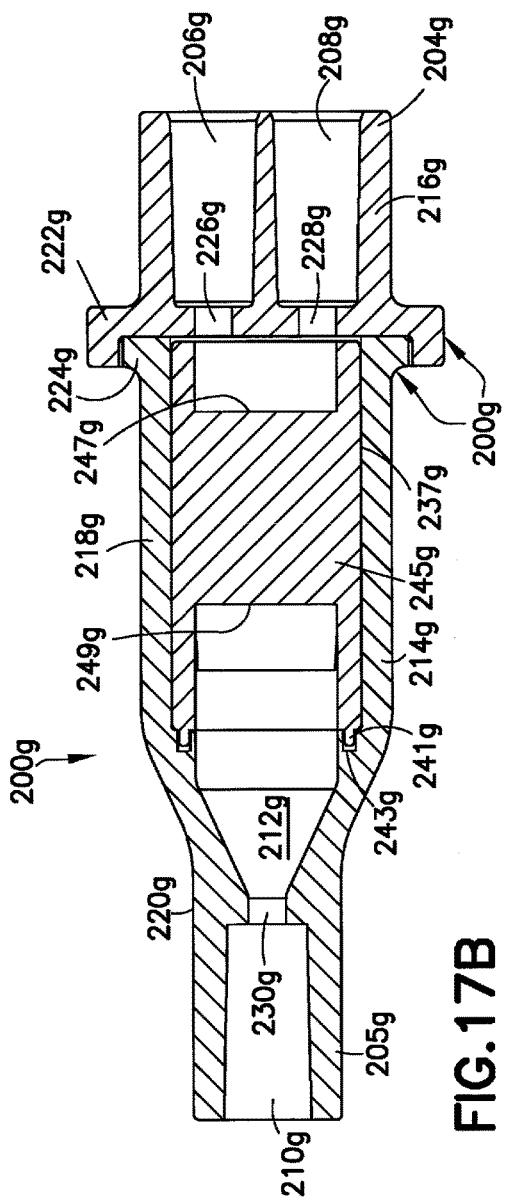
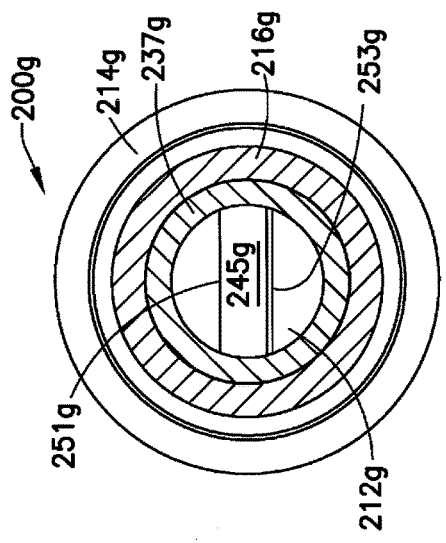
FIG.17B
FIG.17C

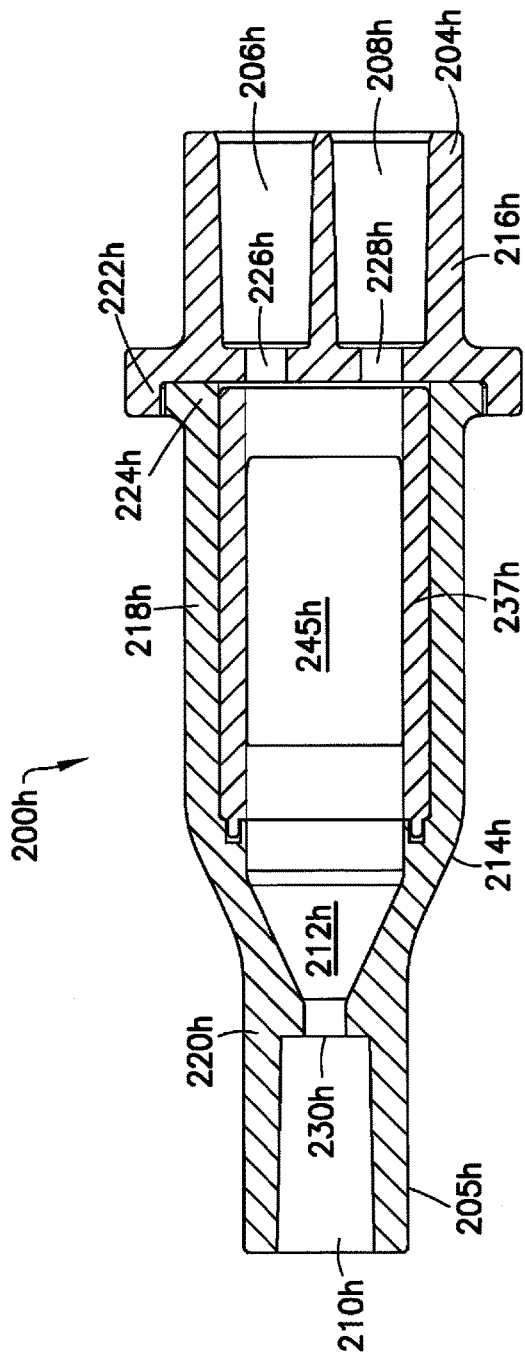
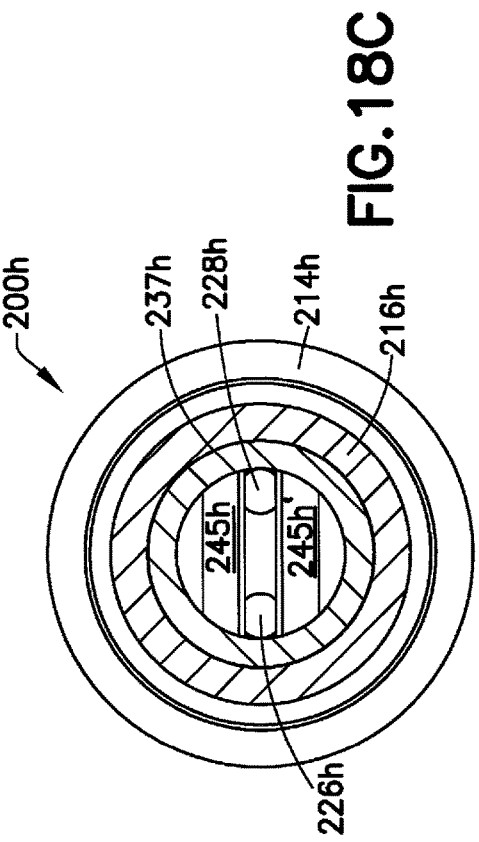
FIG.18B
FIG.18C

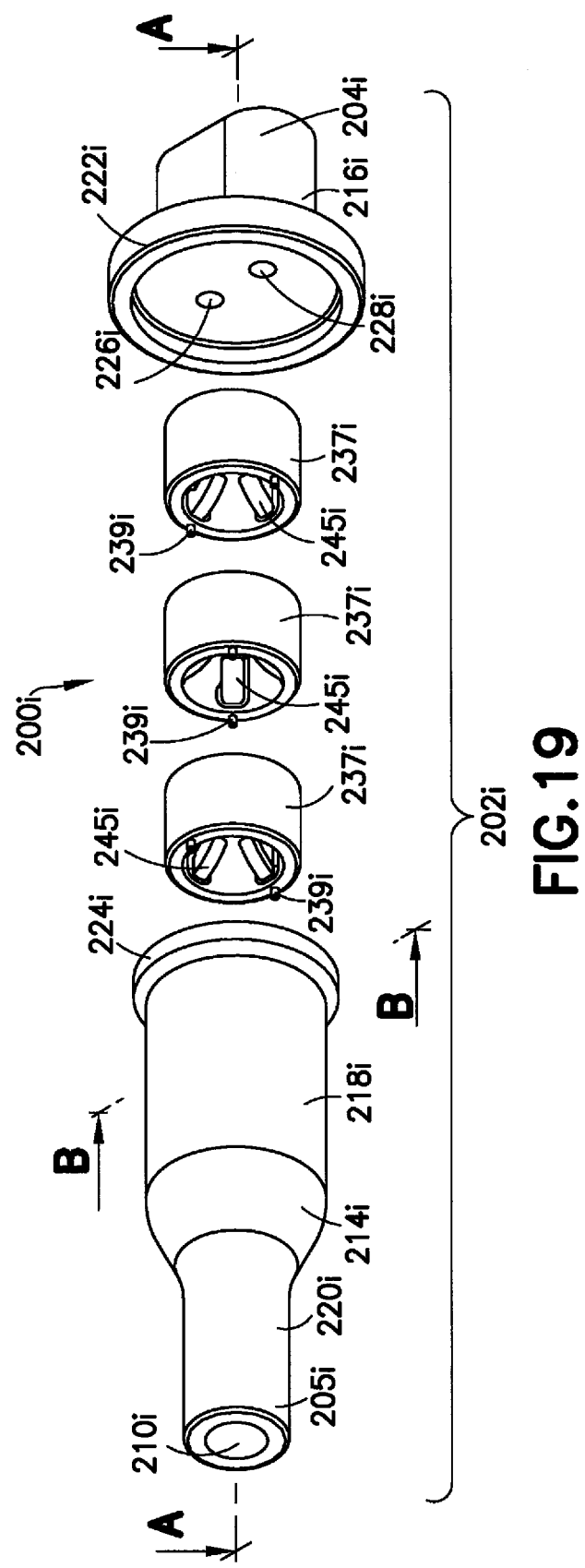

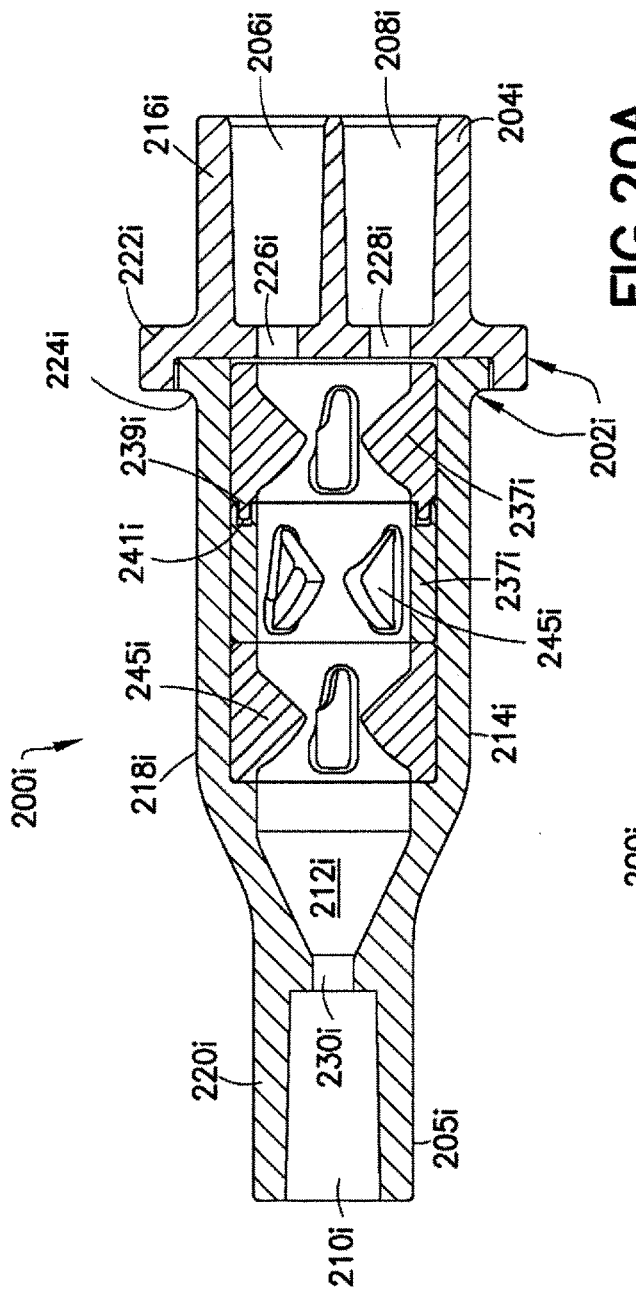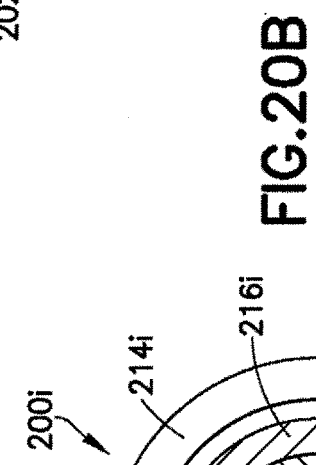

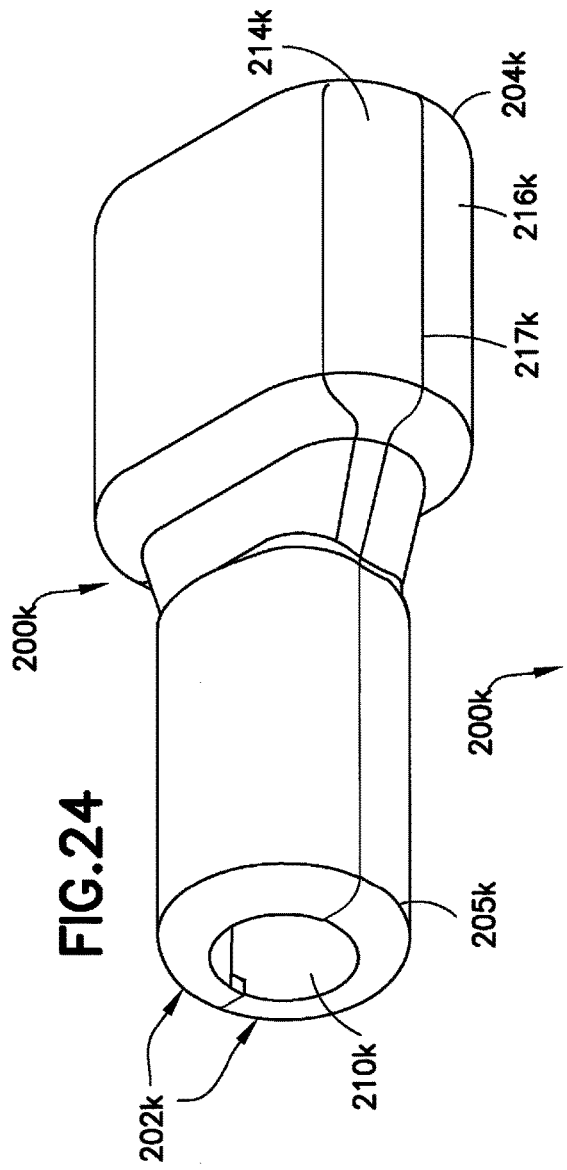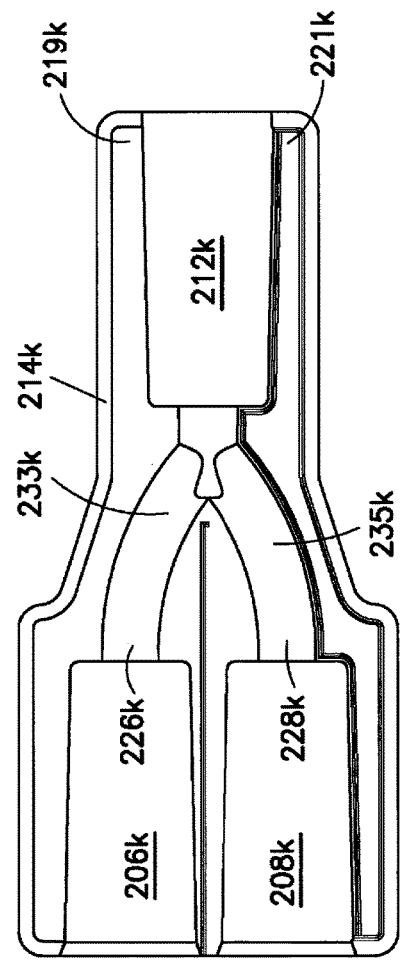

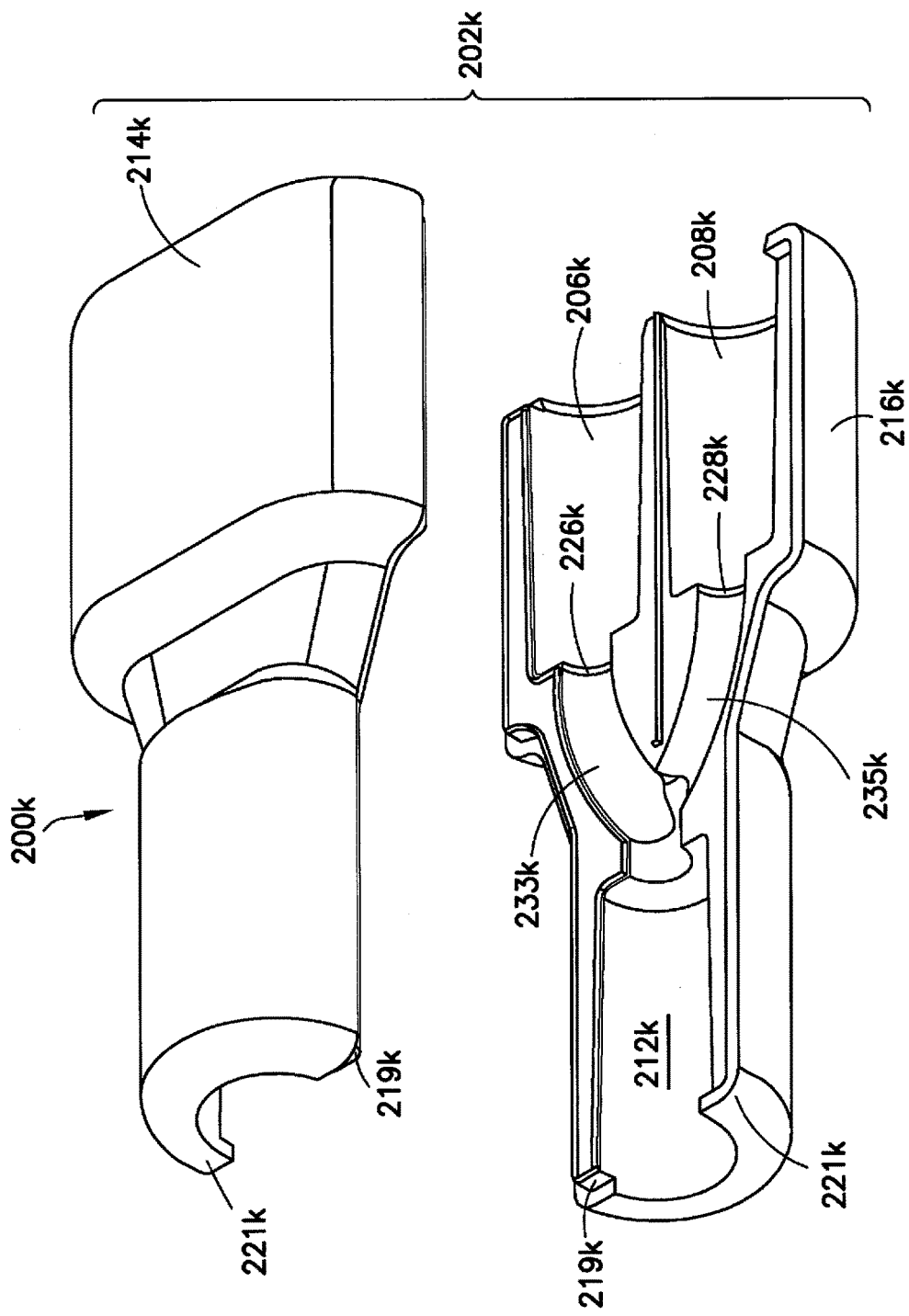

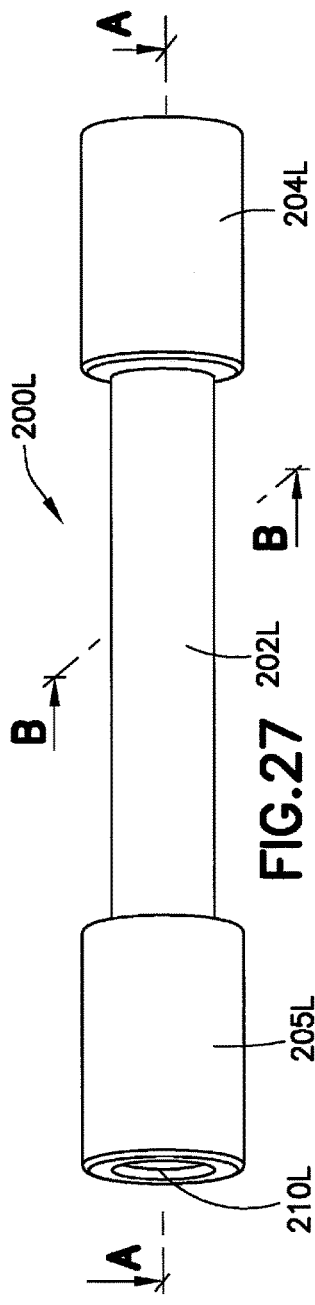
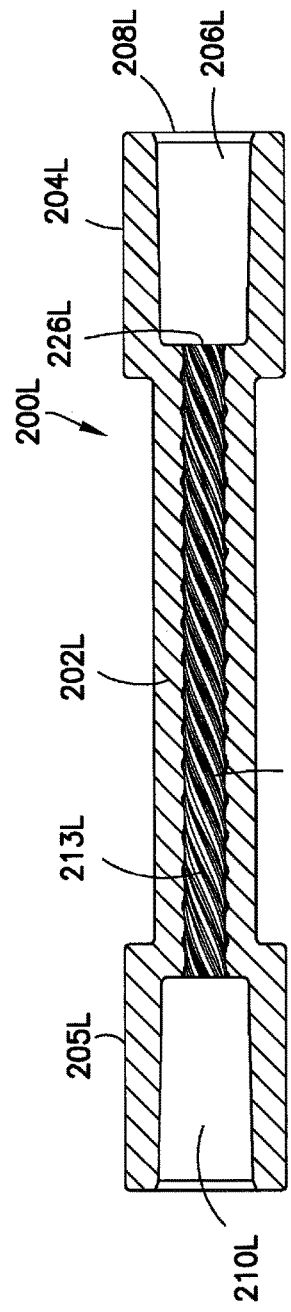
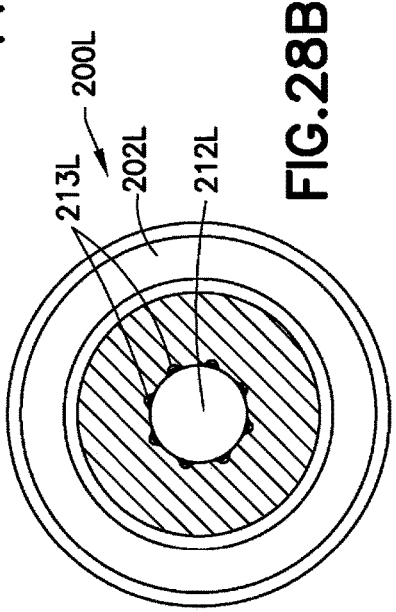
FIG. 27
FIG. 28A
FIG. 28B

FLUID PATH SET WITH TURBULENT MIXING CHAMBER, BACK FLOW COMPENSATOR

CROSS-REFERENCE TO RELATED APPLICATIONS

This application is a Divisional Application of U.S. Ser. No. 13/799,426, filed Mar. 13, 2013, now U.S. Pat. No. 9,555,379, the disclosure of which is incorporated herein in its entirety.

BACKGROUND OF THE INVENTION

Field of the Invention

The invention described herein relates to medical fluid delivery applications and, particularly, to a system for the delivery of one or more medical fluids to a patient using a fluid path set with a turbulent mixing chamber, backflow compensator, and/or air bubble trap.

Description of Related Art

In many medical diagnostic and therapeutic procedures, a medical practitioner, such as a physician, injects a patient with a fluid. In recent years, a number of injector-actuated syringes and powered injectors for pressurized injection of fluids, such as contrast solution (often referred to simply as "contrast"), have been developed for use in procedures such as angiography, computed tomography (CT), ultrasound, and NMR/MRI. In general, these powered injectors are designed to deliver a preset amount of contrast at a preset flow rate.

Angiography is used in the detection and treatment of abnormalities or restrictions in blood vessels. In an angiographic procedure, a radiographic image of a vascular structure is obtained through the use of a radiographic contrast fluid which is injected through a catheter. The vascular structures in fluid connection with the vein or artery in which the contrast is injected are filled with contrast. X-rays passing through the region of interest are absorbed by the contrast, causing a radiographic outline or image of vascular structures containing the contrast. The resulting images can be displayed on, for example, a monitor and recorded.

In a typical angiographic procedure, the medical practitioner places a cardiac catheter into a vein or artery. The catheter is connected to either a manual or to an automatic contrast injection mechanism. A typical manual contrast injection mechanism includes a syringe in fluid connection with a catheter connection. The fluid path also includes, for example, a source of contrast, a source of flushing fluid, typically saline, and a pressure transducer to measure patient blood pressure. In a typical system, the source of contrast is connected to the fluid path via a valve, for example, a three-way stopcock. The source of saline and the pressure transducer may also be connected to the fluid path via additional valves, again such as stopcocks. The operator of the manual contrast injection mechanism controls the syringe and each of the valves to draw saline or contrast into the syringe and to inject the contrast or saline into the patient through the catheter connection.

Automatic contrast injection mechanisms typically include a syringe connected to one or more powered injectors having, for example, a powered linear actuator. Typically, an operator enters settings into an electronic control system of the powered injector for a fixed volume of contrast and saline, and a fixed rate of injection for each. Automatic contrast injection mechanisms provide improved control over manual apparatus where successful use of such manual devices is dependent on the skill of the medical practitioner operating the device. As in a manual system, the fluid path from the automatic contrast injection mechanism to the patient includes, for example, a source of contrast, a source of flushing fluid, typically saline, and a pressure transducer to measure patient blood pressure. The source of contrast is connected to the fluid path via a valve, for example, a three-way stopcock. The source of saline and the pressure transducer may also be connected to the fluid path via additional valves, again such as stopcocks.

When the contrast and the flushing fluid are injected, it is desirable for the two fluids to be mixed well before injection into the patient. However, because the contrast and the flushing fluid typically have different specific gravity and viscosity, the two solutions may not be thoroughly mixed using a known mixing valve, such as a T- or Y-shaped joint, or a three-way stopcock. As a result, when the contrast and the flushing fluid are not mixed properly, the resulting image taken by a fluoroscopic imaging apparatus may be uneven, thereby making it difficult to image the blood vessel clearly. Within the prior art, International Application Publication No. WO 2011/125303 discloses a mixing device for mixing two kinds of fluids. The mixing device includes a first inflow opening and a second inflow opening that is tangential to the first inflow opening to generate a swirling flow as the first and second fluids come into contact. The mixing chamber has a conical shape that is continuously narrowed to an outlet opening. However, existing solutions are often not adequate in promoting thorough mixing of the fluids when small amounts of contrast and flushing solution are introduced and/or when the injection duration is short. Additionally, such existing mixing devices do not compensate for backflow of the contrast or the flushing fluid.

An additional problem with the known multi-fluid injectors is that fluid backflow occurs in injections where a viscous first fluid is injected at a higher ratio than a less viscous second fluid. In such a scenario, before a uniform fluid flow is established, the fluid pressure of the more viscous first fluid that is injected at a higher ratio acts against the fluid pressure of the less viscous second fluid that is injected at a lower ratio to force the second fluid to reverse the desired direction of flow. After injection, pressures equalize, and the fluid injection system achieves a steady state operation where first and second injection fluids are injected at a desired ratio. However, in small volume injections, steady state operation cannot be achieved prior to the completion of the injection process and the total volume of first and second fluids being delivered. Thus, even though a desired ratio of first and second fluids may be 80% first injection fluid to 20% second injection fluid, the actual ratio due to backflow of the first fluid may be higher. This problem is further compounded with an increase in injection pressure. Utilizing check valves downstream of the syringes containing the first and second injection fluids only prevents contamination of the syringes from the backflow and does not address the accuracy of the final mixture ratio.

While manual and automated injectors are known in the medical field, improved fluid delivery systems having a fluid path that promotes turbulent mixing of two or more fluids introduced into a mixing chamber continue to be in demand in the medical field. Additionally, improved fluid transfer sets having a fluid path with a mixing device adapted for thorough fluid mixing are also desired in the medical field. Moreover, the medical field continues to demand improved medical devices and systems used to supply fluids to patients during medical procedures such as angiography, computed tomography, ultrasound, and NMR/MRI.

SUMMARY OF THE INVENTION

While various embodiments of a flow mixing device are described in detail herein, one embodiment may include a housing having a proximal end opposite a distal end, a first fluid port provided at the proximal end of the housing for receiving a first injection fluid, and a second fluid port provided at the proximal end of the housing for receiving a second injection fluid. A mixing chamber may be disposed within the housing between the proximal and distal ends, the mixing chamber being in fluid communication with the first and second fluid ports for mixing the first and second injection fluids. A third fluid port may be provided at the distal end of the housing and in fluid communication with the mixing chamber for discharging a mixed solution of the first and second injection fluids. A turbulent flow inducing member may be disposed within the mixing chamber for promoting turbulent mixing of the first and second injection fluids. The flow mixing device may include a third fluid port for receiving a third injection fluid. The first fluid port and the second fluid port may be substantially parallel with a longitudinal axis of the housing. The first fluid port and the second fluid port may be radially offset from a longitudinal axis of the housing.

In accordance with another embodiment, the turbulent flow inducing member may include a flow dispersion device having at least one deflection member extending over at least a portion of one of the first and second fluid ports for deflecting the fluid flow of the first injection fluid or the second injection fluid from a substantially longitudinal direction to a direction having a radial component. The turbulent flow inducing member may include two deflection members, wherein the first deflection member extends over at least a portion of the first fluid port for deflecting the first injection fluid radially outward with respect to a longitudinal axis of the mixing chamber, and wherein the second deflection member extends over at least a portion of the second fluid port for deflecting the second injection fluid radially outward with respect to the longitudinal axis of the mixing chamber.

In accordance with another embodiment, the turbulent flow inducing member may include at least one turbine wheel having a plurality of rotating blades oriented substantially perpendicular to a direction of fluid flow through the mixing chamber, the at least one turbine wheel being rotatable with respect to a longitudinal axis of the mixing chamber for scattering the first and second injection fluids within the mixing chamber.

In accordance with another embodiment, the turbulent flow inducing member may include a plurality of mixing balls having a diameter larger than a diameter of a smallest of the first, second, and third fluid ports, and wherein the mixing balls are agitated within the mixing chamber by the first and second injection fluids.

In accordance with another embodiment, the turbulent flow inducing member may include a porous filter having a plurality of open cell elements disposed within at least a portion of the mixing chamber.

In accordance with another embodiment, the turbulent flow inducing member may include a disc disposed across a portion of the mixing chamber in a radial direction, the disc having a plurality of recesses extending radially inward from an outer circumference of the disc and at least one opening extending through a central portion of the disc.

In accordance with another embodiment, the turbulent flow inducing member may include a tubular insert fixed within the mixing chamber and at least one hydrofoil element extending across an interior of the tubular insert substantially parallel to a direction of fluid flow through the mixing chamber. The at least one hydrofoil element may have a leading edge oriented toward the proximate end, a trailing edge oriented toward the distal end, an upper chord extending between the leading edge and the trailing edge, and a lower chord extending between the leading edge and the trailing edge opposing the upper chord.

In accordance with another embodiment, the turbulent flow inducing member may include a plurality of tubular flow dispersion members fixed relative to the housing to define the mixing chamber, each of the plurality of flow dispersion members having a plurality of wings extending radially inward from an interior sidewall of the flow dispersion members. The plurality of wings may be spaced apart at equal intervals around the inner circumference of each flow dispersion member, and wherein adjacent flow dispersion members are radially aligned such that the plurality of wings of one flow dispersion member are angularly offset with regard to the plurality of wings of the other flow dispersion member.

In accordance with another embodiment, the turbulent flow inducing member may include two sinusoidal fluid paths extending through the mixing chamber, and wherein the two sinusoidal paths intersect at a plurality of intersection points within the mixing chamber.

In another embodiment, the housing may have a first portion and a second portion joined together at a seam extending around an outer perimeter of the housing between the proximal and distal ends. The seam may include a projection provided on one of the first portion and the second portion and a corresponding groove on the other of the first portion and the second portion for receiving the projection within the groove. The mixing chamber may have a spiral sidewall.

In accordance with another embodiment, the turbulent flow inducing member may include a first arcuate tube in fluid communication with the first fluid port and a second arcuate tube in fluid communication with the second fluid port, wherein the first and second arcuate tubes are curved radially inward toward a central axis of the mixing chamber, and wherein fluid mixing at a juncture between the first and second arcuate tubes is influenced by a Coanda effect.

In a further embodiment, a fluid path set may have a first fluid line having a proximal end and a distal end, where the proximal end of the first fluid line is fluidly connectable to a source of a first injection fluid. The fluid path set may also include a second fluid line having a proximal end and a distal end, where the proximal end of the second fluid line is fluidly connectable to a source of a second injection fluid. A flow mixing device may be in fluid communication with the distal ends of the first and second fluid lines at a proximal end of the flow mixing device. The flow mixing device may include a housing having a proximal end opposite a distal end, a first fluid port provided at the proximal end of the housing for receiving a first injection fluid, and a second fluid port provided at the proximal end of the housing for receiving a second injection fluid. A mixing chamber may be disposed within the housing between the proximal and distal ends, the mixing chamber being in fluid communication with the first and second fluid ports for mixing the first and second injection fluids. A third fluid port may be provided at the distal end of the housing and in fluid communication with the mixing chamber for discharging a mixed solution of the first and second injection fluids. A turbulent flow inducing member may be disposed within the mixing chamber for promoting turbulent mixing of the first and second injection fluids. The flow mixing device may include a third fluid port for receiving a third injection fluid.

In accordance with another embodiment of the fluid path set, the turbulent flow inducing member may include a flow dispersion device having at least one deflection member extending over at least a portion of one of the first and second fluid ports for deflecting the fluid flow of the first injection fluid or the second injection fluid from a substantially longitudinal direction to a direction having a radial component. The turbulent flow inducing member may include two deflection members, wherein the first deflection member extends over at least a portion of the first fluid port for deflecting the first injection fluid radially outward with respect to a longitudinal axis of the mixing chamber, and wherein the second deflection member extends over at least a portion of the second fluid port for deflecting the second injection fluid radially outward with respect to the longitudinal axis of the mixing chamber.

In accordance with another embodiment of the fluid path set, the turbulent flow inducing member may include at least one turbine wheel having a plurality of rotating blades oriented substantially perpendicular to a direction of fluid flow through the mixing chamber, the at least one turbine wheel being rotatable with respect to a longitudinal axis of the mixing chamber for scattering the first and second injection fluids within the mixing chamber.

In accordance with another embodiment of the fluid path set, the turbulent flow inducing member may include a plurality of mixing balls having a diameter larger than a diameter of a smallest of the first, second, and third fluid ports, and wherein the mixing balls are agitated within the mixing chamber by the first and second injection fluids.

In accordance with another embodiment of the fluid path set, the turbulent flow inducing member may include a porous filter having a plurality of open cell elements disposed within at least a portion of the mixing chamber.

In accordance with another embodiment of the fluid path set, the turbulent flow inducing member may include a disc disposed across a portion of the mixing chamber in a radial direction, the disc having a plurality of recesses extending radially inward from an outer circumference of the disc and at least one opening extending through a central portion of the disc.

In accordance with another embodiment of the fluid path set, the turbulent flow inducing member may include a tubular insert fixed within the mixing chamber and at least one hydrofoil element extending across an interior of the tubular insert substantially parallel to a direction of fluid flow through the mixing chamber. The at least one hydrofoil element may have a leading edge oriented toward the proximate end, a trailing edge oriented toward the distal end, an upper chord extending between the leading edge and the trailing edge, and a lower chord extending between the leading edge and the trailing edge opposing the upper chord.

In accordance with another embodiment of the fluid path set, the turbulent flow inducing member may include a plurality of tubular flow dispersion members fixed relative to the housing to define the mixing chamber, each of the plurality of flow dispersion members having a plurality of wings extending radially inward from an interior sidewall of the flow dispersion members. The plurality of wings may be spaced apart at equal intervals around the inner circumference of each flow dispersion member, and wherein adjacent flow dispersion members are radially aligned such that the plurality of wings of one flow dispersion member are angularly offset with regard to the plurality of wings of the other flow dispersion member.

In accordance with another embodiment, the turbulent flow inducing member may include two sinusoidal fluid paths extending through the mixing chamber, and wherein the two sinusoidal paths intersect at a plurality of intersection points within the mixing chamber.

In another embodiment of the fluid path set, the housing of the fluid mixing device may have a first portion and a second portion joined together at a seam extending around an outer perimeter of the housing between the proximal and distal ends. The seam may include a projection provided on one of the first portion and the second portion and a corresponding groove on the other of the first portion and the second portion for receiving the projection within the groove. The mixing chamber may have a spiral sidewall.

In accordance with another embodiment of the fluid path set, the turbulent flow inducing member may include a first arcuate tube in fluid communication with the first fluid port and a second arcuate tube in fluid communication with the second fluid port, wherein the first and second arcuate tubes are curved radially inward toward a central axis of the mixing chamber, and wherein fluid mixing at a juncture between the first and second arcuate tubes is influenced by a Coanda effect.

In a further embodiment, a method of mixing a drug solution may include the steps of delivering a first injection fluid to a flow mixing device, delivering a second injection fluid to the flow mixing device, mixing the first and second injection fluids inside a mixing chamber of the flow mixing device, and delivering a mixed solution of the first and second injection fluids from the flow mixing device. The mixing chamber of the flow mixing device may include a turbulent flow inducing member for promoting turbulent mixing of the first and second injection fluids.

In accordance with a further embodiment, a method for capacitance volume correction in a multi-fluid delivery system may include pressurizing a first expandable body having a first injection fluid by reducing the volume in the first expandable body with movement of a first pressurizing element and pressurizing a second expandable body having a second injection fluid by reducing the volume in the second expandable body with movement of a second pressurizing element. The method may further include controlling an acceleration of the first pressurizing element relative to the acceleration of the second pressurizing element as a function of relative velocities of the first and second pressurizing elements and a capacitance correction factor for correcting for volume expansion of the first and second expandable bodies. Movement of the first and second pressurizing elements may be controlled with an algorithm. The first expandable body may be pressurized to a first pressure, and the second expandable body may be pressurized to a second pressure. In one embodiment, the first pressure may be higher than the second pressure. The capacitance correction factor may be a function of the volume in the first and second expandable bodies, and a pressure inside the first and second expandable bodies. The velocity of the first pressurizing member may be higher than the velocity of the second pressurizing member.

In another embodiment, a method for capacitance volume correction in a multi-fluid delivery system may include the steps of pressurizing a first syringe having a first injection fluid to a first pressure by reducing the volume in the first syringe with movement of a first piston at a first acceleration and pressurizing a second syringe having a second injection fluid to the first pressure by reducing the volume in the second syringe with movement of a second piston at a second acceleration different from the first acceleration. The acceleration of the first piston relative to the acceleration of the second piston may be a function of a capacitance correction factor for correcting volume expansion of the first and second syringes. The capacitance correction factor may be a function of the volume in the first and second syringes, and the first pressure.

These and other features and characteristics of the fluid path set with a turbulent mixing chamber, as well as the methods of manufacture and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

BRIEF DESCRIPTION OF THE DRAWINGS

FIG. 6B is a cross-sectional view of the flow mixing device taken along line B-B shown in FIG. 4.

FIG. 6C is a cross-sectional view of the flow mixing device taken along line C-C shown in FIG. 4

FIG. 8A is a cross-sectional view of an assembled flow mixing device taken along line A-A shown in FIG. 7.

FIG. 8B is a cross-sectional view of an assembled flow mixing device taken along line B-B shown in FIG. 7.

FIG. 8C is a cross-sectional view of an assembled flow mixing device taken along line C-C shown in FIG. 7.

FIG. 8D is a cross-sectional view of an assembled flow mixing device taken along line D-D shown in FIG. 7.

FIG. 16 is an exploded perspective view of the flow mixing device shown in FIG. 15.

FIG. 17A is a cross-sectional view of an assembled flow mixing device taken along line A-A shown in FIG. 15.

FIG. 17B is a cross-sectional view of an assembled flow mixing device taken along line B-B shown in FIG. 15.

FIG. 17C is a cross-sectional view of an assembled flow mixing device taken along line C-C shown in FIG. 15.

FIG. 18B is a cross-sectional view of the flow mixing device shown in FIG. 18A.

FIG. 18C is a cross-sectional view of the flow mixing device shown in FIG. 18A.

FIG. 19 is an exploded perspective view of a flow mixing device in accordance with a ninth embodiment.

FIG. 20A is a cross-sectional view of the flow mixing device taken along line A-A shown in FIG. 19.

FIG. 20B is a cross-sectional view of an assembled flow mixing device taken along line B-B shown in FIG. 19.

FIG. 24 is a top perspective view of a flow mixing device in accordance with an eleventh embodiment.

FIG. 25 is an exploded perspective view of the flow mixing device shown in FIG. 24.

FIG. 26 is a top view of a first portion of the flow mixing device shown in FIG. 25.

FIG. 27 is a top perspective view of a flow mixing device in accordance with a twelfth embodiment.

FIG. 28A is a cross-sectional view of the flow mixing device taken along line A-A shown in FIG. 27.

FIG. 28B is a cross-sectional view of the flow mixing device taken along line B-B shown in FIG. 27.

DESCRIPTION OF THE PREFERRED EMBODIMENTS

For purposes of the description hereinafter, spatial orientation terms, as used, shall relate to the referenced embodiment as it is oriented in the accompanying drawing figures or otherwise described in the following detailed description.

However, it is to be understood that the embodiments described hereinafter may assume many alternative variations and configurations. It is also to be understood that the specific components, devices, and features illustrated in the accompanying drawing figures and described herein are simply exemplary and should not be considered as limiting.

Figure 1:
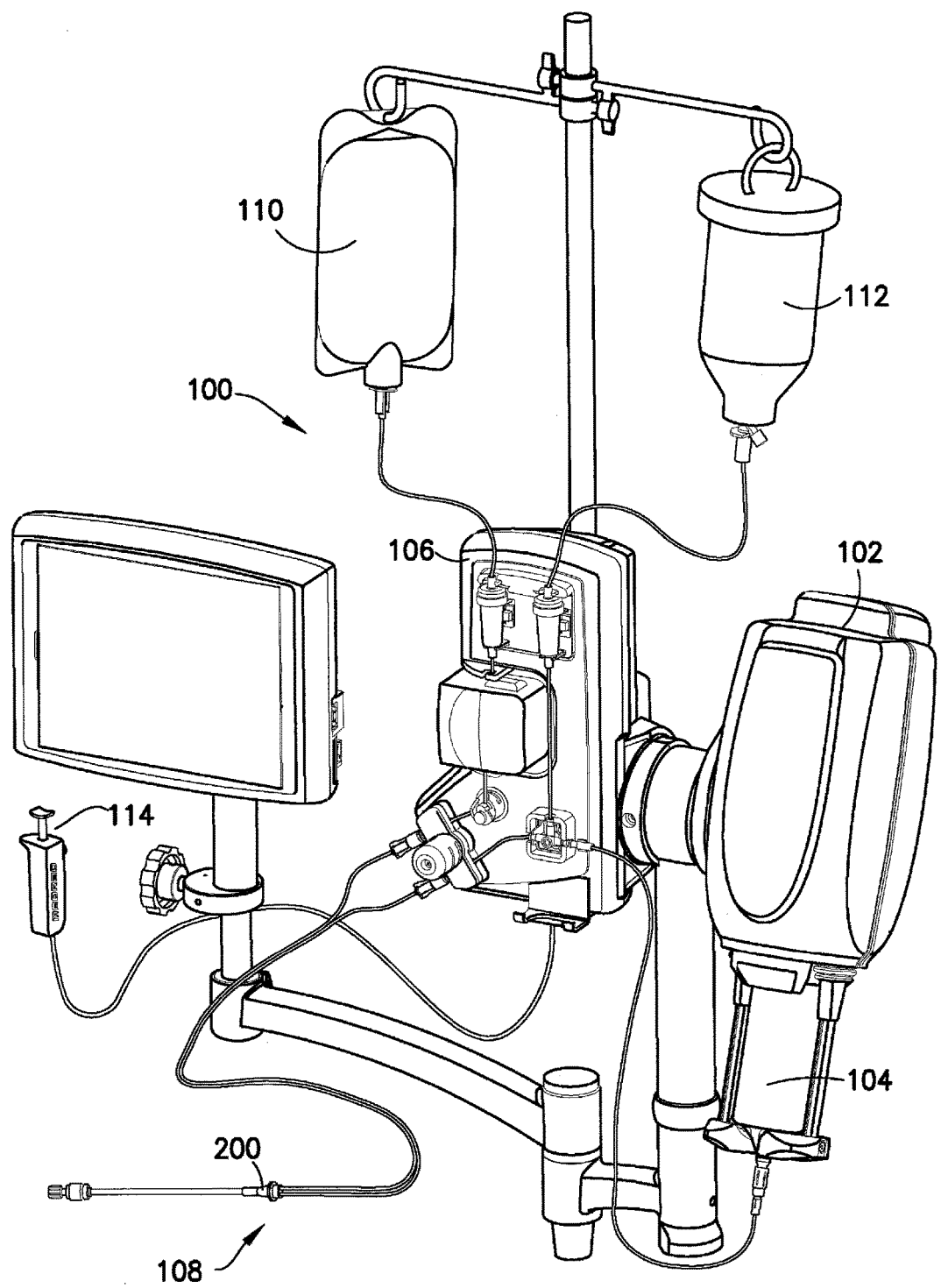
FIG. 1 is a perspective view of a fluid delivery system according to one embodiment.

FIG. 1 is a perspective view of a fluid delivery system 100 having a flow mixing device 200 according to one embodiment. The fluid delivery system 100 is adapted for delivering fluids to a patient during a medical injection procedure. For example, the fluid delivery system 100 may be used during an angiographic procedure to inject contrast solution and common flushing agents, such as saline, into the body of a patient. An example of such a fluid injection or delivery system is disclosed in U.S. patent application Ser. No. 09/982,518, filed on Oct. 18, 2001, now issued as U.S. Pat. No. 7,094,216 on Aug. 22, 2006 (hereinafter "the '216 patent"), and assigned to the assignee of the present application, the disclosure of which is incorporated herein by reference in its entirety. Additional examples of fluid delivery systems are disclosed in the following references: U.S. patent application Ser. No. 10/825,866, filed on Apr. 16, 2004, now issued U.S. Pat. No. 7,556,619 on Jul. 7, 2009 (hereinafter "the '619 patent"); U.S. Pat. No. 8,337,456 to Schriver et al., issued Dec. 25, 2012; U.S. Pat. No. 8,147,464 to Spohn et al., issued Apr. 3, 2012; and, U.S. patent application Ser. No. 11/004,670, now published as U.S. 2008/0086087 on Apr. 10, 2008, each of which are assigned to the assignee of the present application and the disclosures of which are incorporated herein by reference in their entireties. The flow mixing device 200 is generally adapted to interface with one or more components of the fluid delivery system 100 to aid in the mixing of the fluids, particularly contrast solution and saline solution in the case of angiographic procedures, to be delivered to the patient.

The fluid delivery system 100 generally includes a powered fluid injector 102 that is adapted to support and actuate a syringe 104 storing a first injection fluid for injection to a patient during a medical procedure, such as an angiographic procedure. The fluid delivery system 100 further includes a second injection fluid that may be mixed with the first injection fluid prior to being delivered to a patient. The injector 102 is generally used to supply the first and second injection fluids under pressure to the fluid path set 108 and, ultimately, the patient. The injector 102 may be controlled by a hand controller 114 to supply the first and second injection fluids at discrete and preselected flow rates based on the physical inputs to the hand controller 114.

The following operational discussion of the flow mixing device 200 will be with exemplary reference to an angiographic procedure involving the fluid delivery system 100 and how the flow mixing device 200 contributes to the homogeneous mixing of the first injection fluid and the second injection fluid from the fluid delivery system 100. In typical angiographic procedures, the first injection fluid is contrast solution and the second injection fluid or flushing agent is saline. The contrast solution typically has higher viscosity and specific gravity compared to saline. One of ordinary skill in the art will appreciate that, depending on the medical procedure, various other medical fluids can be used as the first injection fluid and the second injection fluid.

The injector 102 is operatively associated with a fluid control module 106. The fluid control module 106 may be adapted for controlling the operation of the fluid delivery system 100 by allowing the user to manually select the injection parameters, or select a pre-defined injection protocol. Alternatively, this functionality may reside with an external control unit or with the powered injector 102. In either case, the fluid control module 106 controls the injection pressure and the ratio of the first injection fluid relative to the second injection fluid. The fluid control module 106 is generally adapted to support a fluid path set 108 that is generally adapted to fluidly connect the syringe 104 to a source of first injection fluid (contrast solution) 112. The fluid path set 108 is further connected to a source of second injection fluid (saline) 110 which is supplied to the patient via the same catheter as the contrast solution. The flow mixing device 200 is disposed within the fluid path set 108 and is adapted for mixing the fluids from the syringe 104 and the source of saline 110. The flow of the contrast solution from the syringe 104 and the saline is regulated by the fluid control module 106 which controls the various valves and flow regulating structures in the fluid path set 108 to regulate the delivery of contrast solution and saline to the patient based on user selected injection parameters, such as total injection volume and ratio of contrast solution and saline. The fluid path set 108 further connects the syringe 104 to a catheter (not shown) which is associated with the patient for supplying the contrast solution and saline to the patient.

Figure 2:
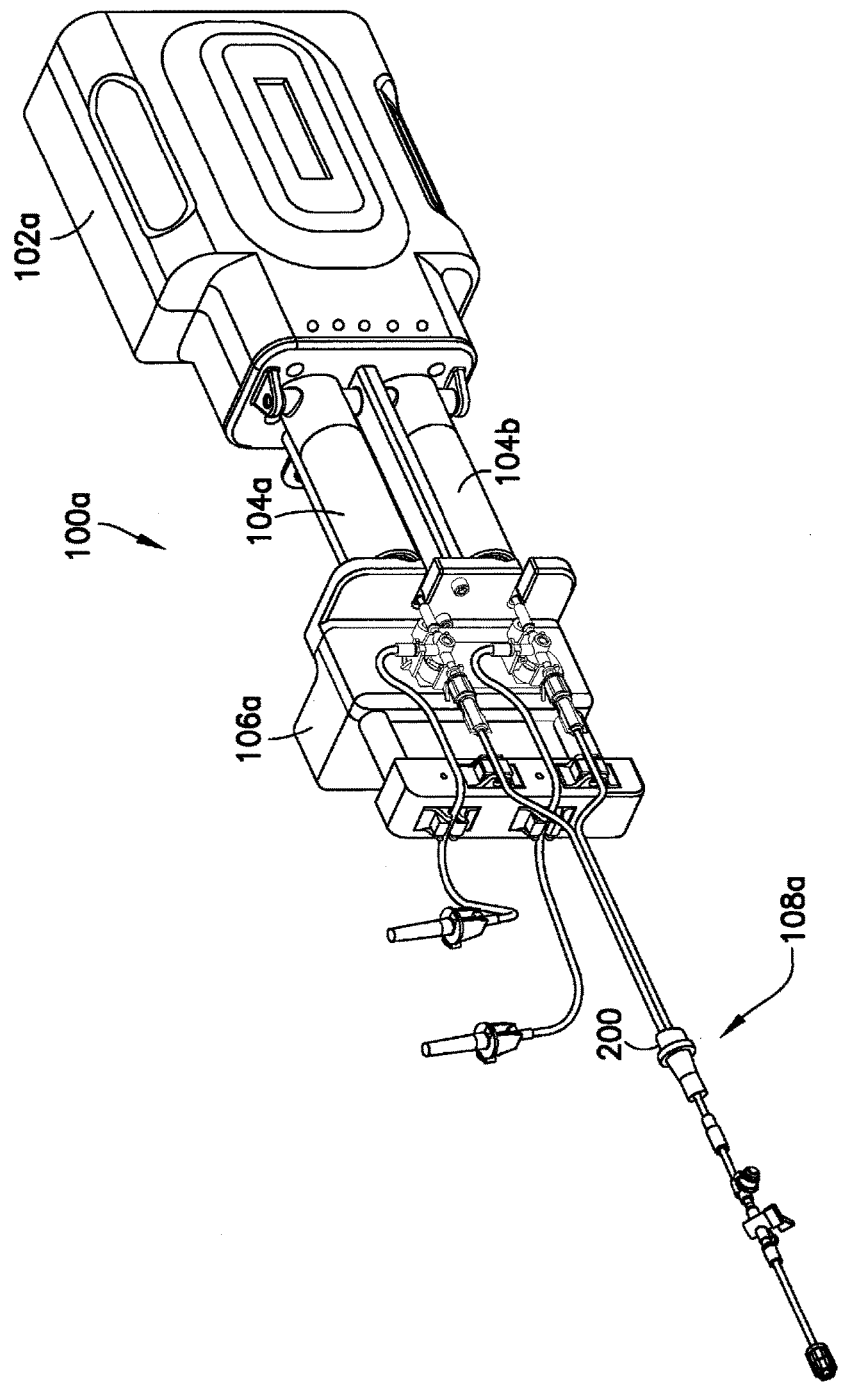
FIG. 2 is a perspective view of a fluid delivery system according to another embodiment.

FIG. 2 illustrates an alternative embodiment of fluid delivery system 100a having a powered fluid injector 102a adapted to interface with two syringes 104a, 104b which may be fluidly connected to a source of first injection fluid (not shown) and a source of second injection fluid (not shown) or any two desired medical fluids. Injector 102a is desirably at least a dual-syringe injector, wherein two fluid delivery syringes are oriented in a side-by-side relationship and which are separately actuated by respective piston elements associated with the injector 102a. Fluid path set 108a may be interfaced with injector 102a in a similar manner to that described previously in connection with fluid delivery system 100 described with reference to FIG. 1. In particular, the injector 102a is operatively associated with a fluid control module 106a. The fluid control module 106a is generally adapted to support a fluid path set 108a that is generally adapted to fluidly connect to the first syringe 104a having a first injection fluid, such a contrast solution. The fluid path set 108a is further connected to the second syringe 104b having a second injection fluid, such as saline. The flow mixing device 200 is disposed within the fluid path set 108a and is adapted for mixing the fluid flow from the first and second syringe 104a, 104b. The flow of the first injection fluid from the first syringe 104a and the second injection fluid from the second syringe 104b is regulated by a fluid control module 106a which controls the various valves and flow regulating structures to regulate the delivery of first and second medical fluids to the patient based on user selected injection parameters, such as total injection volume and ratio of contrast solution and saline. The fluid path set 108a further connects to a catheter (not shown) which is associated with the patient for supplying the first and second medical fluids to the patient. A suitable multi-syringe fluid injector for use with the above-described system is described in U.S. patent application Ser. No. 13/386,765, filed on Jan. 24, 2012, which published as U.S. Patent Application Publication No. 2012/0123257, and is assigned to the assignee of the present application, the disclosure of which is incorporated herein by reference in its entirety. Other relevant multi-fluid delivery systems are found in U.S. patent application Ser. No. 10/159,592, filed on May 30, 2002 (published as U.S. 2004/0064041), U.S. patent application Ser. No. 10/722,370, filed Nov. 25, 2003 (published as U.S. 2005/0113754), and International Patent Application No. PCT/US2012/037491, filed on May 11, 2012 (published as WO 2012/155035), all of which are assigned to the assignee of the present application, and the disclosures of which are incorporated herein by reference.

In another embodiment, a manually-controlled fluid delivery system (not shown) may be provided. Similar to power-operated fluid delivery systems described with reference to FIGS. 1-2, a manually-controlled fluid delivery system may include a first injector adapted to actuate a first syringe storing a first injection fluid, such as a contrast medium, for injection to a patient during a medical procedure. The manually-controlled fluid delivery system may also include a second injector adapted to actuate a second syringe storing a second injection fluid, such as saline. A fluid path set is provided for delivering and mixing the first injection fluid and the second injection fluid in a desired ratio prior to being delivered to a patient. An exemplary manually-controlled fluid delivery system is disclosed in U.S. patent application Ser. No. 13/755,883, filed Jan. 31, 2013, assigned to the assignee of the present application, the disclosure of which is incorporated herein by reference.

Figure 3:
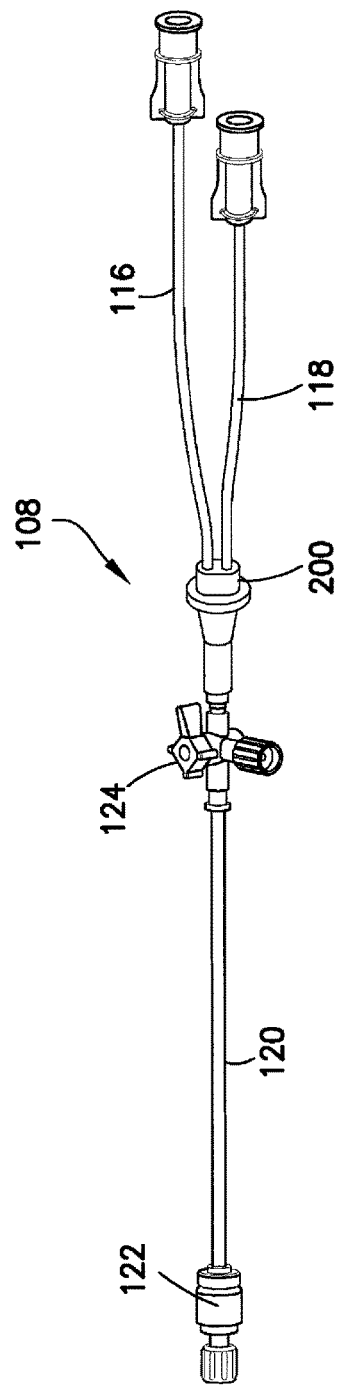
FIG. 3 is a top perspective view of a fluid path for use in a fluid delivery system.

With reference to FIG. 3, fluid path set 108 is shown removed from the fluid delivery system. The fluid path set 108 includes a first fluid line 116 in fluid communication at its proximal end with the source of the first injection fluid and a second fluid line 118 in fluid communication at its proximal end with the source of the second injection fluid. First and second fluid lines 116, 118 act as fluid conduits for delivering the first and second injection fluid, respectively, from the source of each respective fluid. Distal ends of each of the first and second fluid lines 116, 118 are in fluid communication with the flow mixing device 200. First and second injection fluids flow into the mixing device 200 and mix in the mixing device 200. In one embodiment, a contrast medium having a high specific gravity is delivered under pressure to the mixing device 200 through the first fluid line 116 and a saline solution having a lower specific gravity relative to the contrast medium is delivered under pressure to the mixing device 200 through the second fluid line 118. Then, the mixed solution of the first and second injection fluid is passed through a third fluid line 120 in fluid connection at its proximal end with a distal end of the flow mixing device 200. A distal end of the third fluid line 120 is desirably connected to a catheter by a connector 122 to deliver the mixed solution of the first and second injection fluid to the patient. The connector 122 may be bonded to the third fluid line 120 by a conventional UV bonding technique. Alternatively, the connector 122 may be coupled to the third fluid line 120 by an over-molding technique. While FIG. 3 illustrates the connector 122 being provided on the third fluid line 120, the connector 122 may be provided on any one or all of the first, second, and third fluid lines 116, 118, 120, respectively. One or more valves 124 may be provided within the fluid path set 108 to selectively block the passage of first and/or second injection fluid through the fluid path set 108. For example, a one-way valve may be provided on one or both of the first and second fluid lines 116, 118, respectively, to prevent the first or second injection fluid to flow back into the source of the first and second injection fluid. Alternatively, or in addition, the one-way valve may be provided on the third fluid line 120 to prevent the mixed solution of the first and second injection fluids to flow back into the flow mixing device 200. In one embodiment, the one or more valves 124 may be provided directly on the flow mixing device 200.

With reference to FIGS. 4, 5, and 6A-6C, a flow mixing device 200a is illustrated in accordance with a first embodiment. Flow mixing device 200a includes a housing 202a having a proximal end 204a opposite a distal end 205a. The proximal end 204a of the housing 202a includes a first fluid port 206a and a second fluid port 208a (shown in FIG. 6A) which are connected or connectable to respective first fluid line 116 and second fluid line 118 (not shown). The proximal end 204a of the housing 202a may include a connector (not shown) for connecting the first and second fluid lines 116, 118 to the flow mixing device 200a. The distal end 205a of the housing 202a includes a third fluid port 210a which is connected or connectable to the third fluid line 120. The distal end 205a of the housing 202a may include a connector (not shown) for connecting the flow mixing device 200a to the third fluid line 120 or to a catheter.

The housing 202a of the flow mixing device 200a defines a mixing chamber 212a (shown in FIG. 6A) where first and second injection fluids mix to form a mixed solution. The mixing chamber 212a is adapted for providing a homogenous mixing flow under turbulent conditions to promote a thorough mixing of the first and second injection fluids and produce a substantially homogeneous mixed solution. Additionally, the mixing chamber 212a is also adapted to eliminate zones of stagnant fluid flow. The housing 202a is desirably formed from a medical-grade plastic material having sufficient rigidity to prevent any substantial expansion of the housing 202a during the injection procedure. For example, the housing 202a is adapted to retain its shape without appreciable expansion in volume at an injection pressure of 1200 psi.

Figure 4:
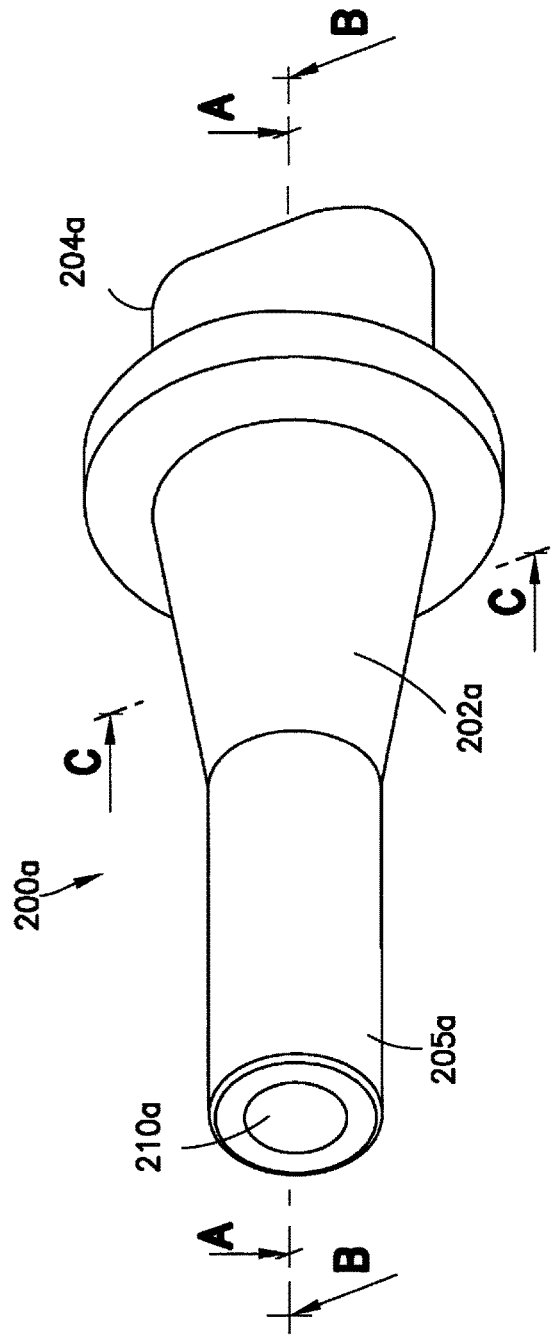
FIG. 4 is a top perspective view of a flow mixing device in accordance with a first embodiment.
Figure 5:
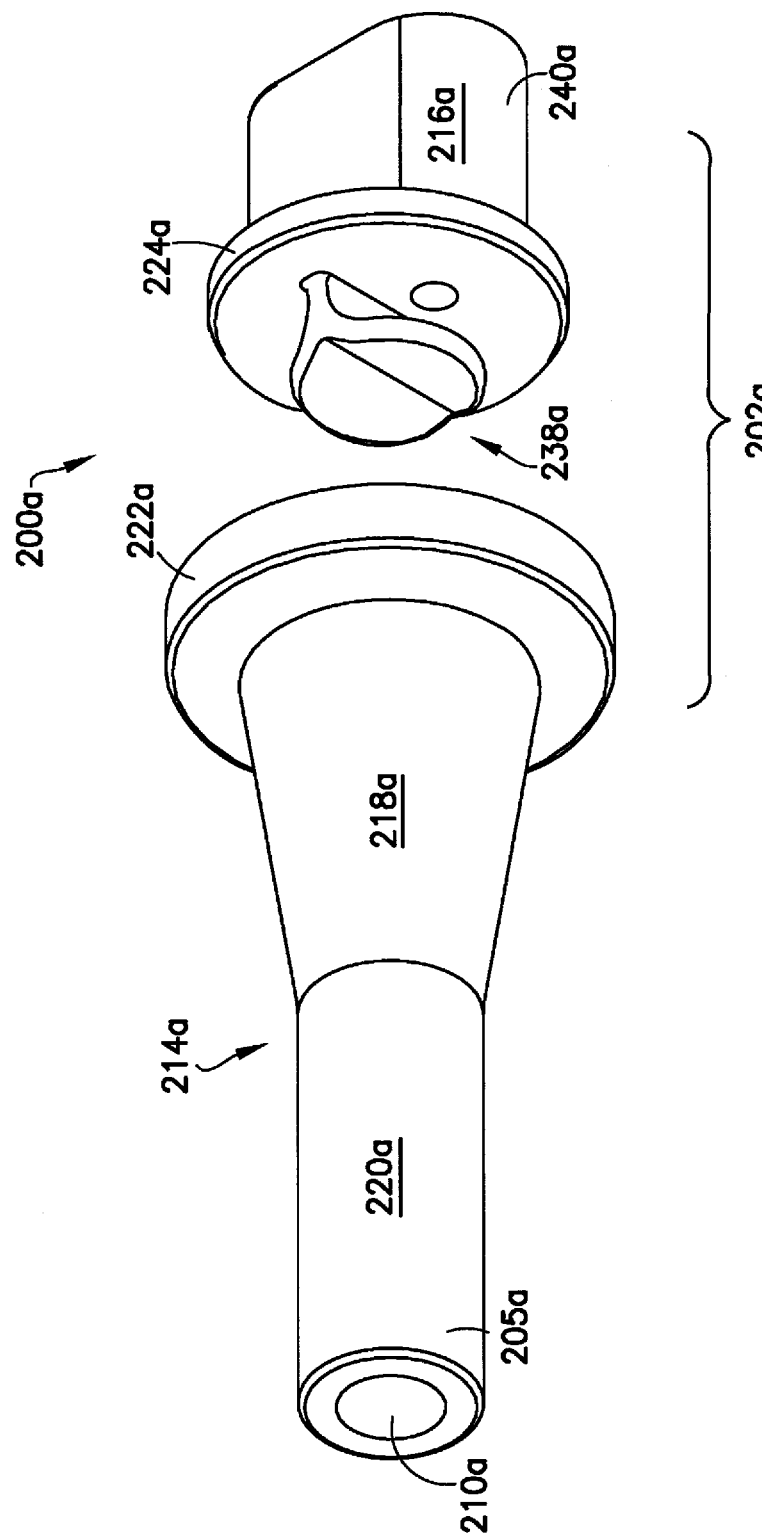
FIG. 5 is an exploded perspective view of the flow mixing device shown in FIG. 4.

With specific reference to FIG. 5, and with continuing reference to FIG. 4, the housing 202a of the flow mixing device 200a includes a first portion 214a and second portion 216a. The first portion 214a of the housing 202a has a substantially conical proximal end 218a and a substantially cylindrical distal end 220a. A collar 222a surrounds the base of the conical proximal end 218a of the first portion 214a. The second portion 216a includes a flange 224a that corresponds to the collar 222a of the first portion 214a to receive the flange 224a within the collar 222a. In another embodiment, the collar 222a is provided on the second portion 216a, while the flange 224a is provided on the first portion 214a of the housing 202a. In one preferred and non-limiting embodiment, the first and second portions 214a, 216a are permanently coupled together by gluing, ultrasonic welding, an interference fit connection, or other mechanical securing arrangement.

Figure 6A:
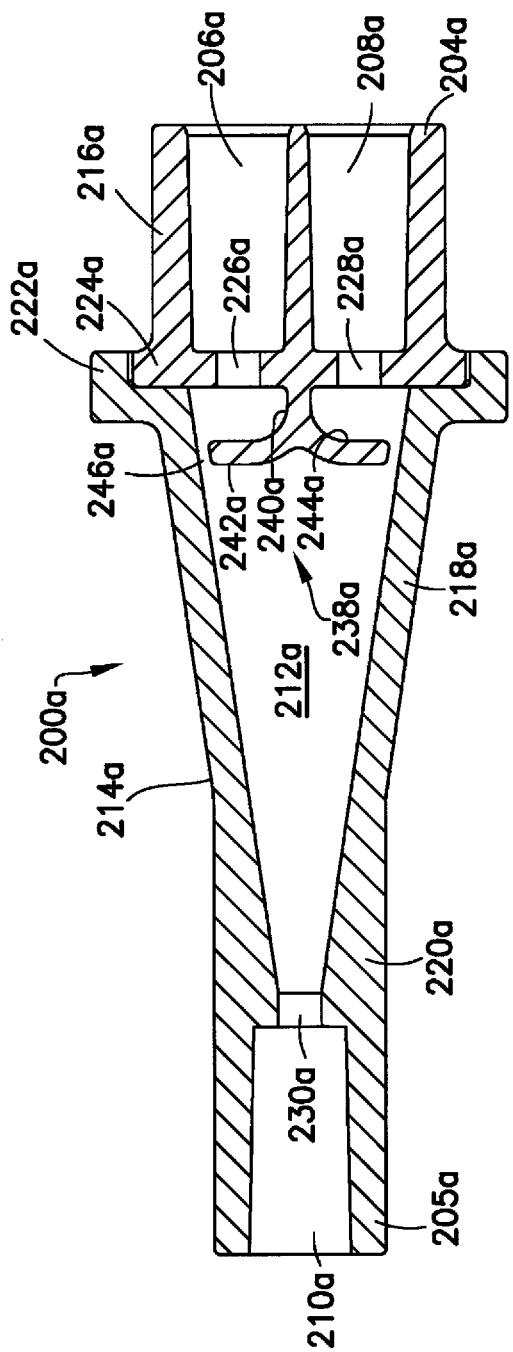
FIG. 6A is a cross-sectional view of the flow mixing device taken along line A-A shown in FIG. 4.

With reference to FIGS. 6A-6C, and with continuing reference to FIG. 5, the first and second fluid ports 206a, 208a extend through the second portion 216a and are in fluid communication with the mixing chamber 212a through first and second fluid orifices 226a, 228a, respectively. First and second fluid ports 206a, 208a are substantially parallel to each other. In other embodiments, first and second fluid ports 206a, 208a may be angled relative a longitudinal axis of flow mixing device 200a such that fluid flow of the first and second injection fluids converges or diverges relative to the longitudinal axis. In one exemplary embodiment, a contrast medium may be supplied through the first fluid port 206a and saline may be supplied through the second fluid port 208a. Fluid flowing through the first and second fluid ports 206a, 208a passes through the first and second fluid orifices 226a, 228a having a reduced cross-section relative to the first and second fluid ports 206a, 208a. First and second fluid orifices 226a, 228a have equal diameters. In another embodiment, the diameter of the first fluid orifice 226a may be larger or smaller relative to the diameter of the second fluid orifice 228a. First and second injection fluids mix within the mixing chamber 212a to form a mixed solution. The mixed solution is discharged from the mixing chamber 212a through a third fluid orifice 230a provided at a distal end of the first portion 214a of the housing 202a. The third fluid orifice 230a is in fluid communication with the third fluid port 210a that discharges the mixed fluid from the mixing device 200a through a fluid conduit (not shown).

As best shown in FIGS. 6A and 6B, the mixing chamber 212a is defined within the interior of the first portion 214a. The mixing chamber 212a has a generally conical shape that narrows from the proximal end 218a to the distal end 220a such that a cross-sectional shape of the mixing chamber 212a is substantially circular (FIG. 6C). Alternatively, the cross-sectional shape of the mixing chamber 212a may be an ellipse or any other shape formed from a curved line. In another embodiment, the mixing chamber 212a may have a first portion that narrows from the proximal end 218a to the distal end 220a and a substantially cylindrical portion that extends therefrom.

With continuing reference to FIGS. 6A-6C, second portion 216a includes a fluid flow dispersion device 238a having a stem 240a and two deflection members 242a, 244a. The stem 240a is positioned between the first and second fluid orifices 226a, 228a and extends in a longitudinal direction toward the distal end 220a of the first portion 214a. Deflection members 242a, 244a extend radially outward from the stem 240a. A transitional portion between a longitudinally-extending stem 240a and the radially-extending deflection members 242a, 244a is curved to gradually transition the flow of the first and second injection fluid from a substantially longitudinal direction to a substantially radial direction with respect to a central axis of the mixing chamber. A radial space 246a is provided between the terminal end of each deflection member 242a, 244a and the sidewall of the mixing chamber 212a. First and second injection fluids are deflected to flow from a substantially longitudinal direction to a substantially radial direction by the deflection members 242a, 244a and are forced to flow through the radial space 246a. The rapid change in the flow direction of the first and second injection fluids promotes turbulent mixing of the first injection fluid and the second injection fluid within the mixing chamber 212a.

Figure 7:
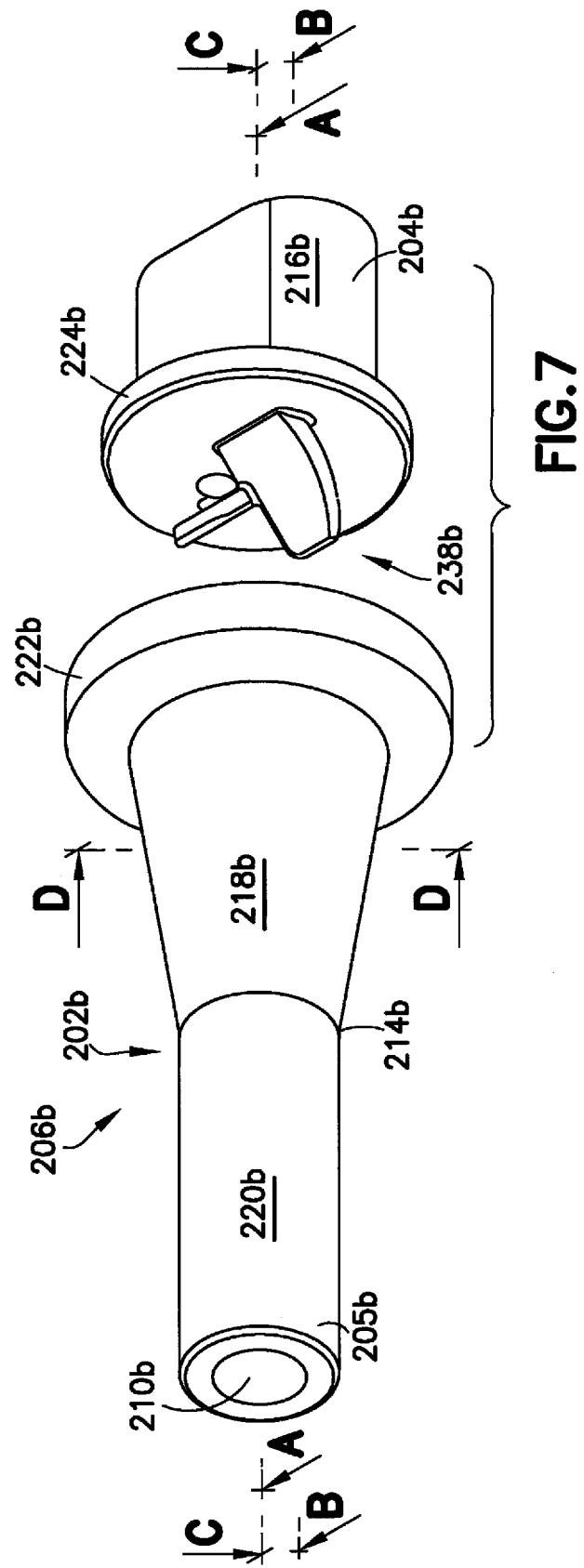
FIG. 7 is an exploded perspective view of a flow mixing device in accordance with a second embodiment.

With reference to FIGS. 7-8D, a flow mixing device 200b is illustrated in accordance with a second embodiment. The housing 202b of the flow mixing device 200b is substantially similar to the housing 202a of the flow mixing device 200a described above. Reference numerals 200b-230b in FIG. 7 are used to illustrate identical components as reference numerals 200a-230a in FIGS. 4-5. As the previous discussion regarding the flow mixing device 200a generally shown in FIGS. 4-6C is applicable to the embodiment shown in FIGS. 7-8D, only the relevant differences between these systems are discussed hereinafter.

With specific reference to FIGS. 8A-8D, second portion 216b includes two deflection members 242b, 244b extending radially outward over first and second fluid orifices 228a, 228b in mutually opposing directions. First injection fluid is directed in one radial direction by the first deflection member 242b, while the second injection fluid is directed in the opposite radial direction by the second deflection member 244b. A radial space 246b is provided between the terminal end of each deflection member 242b, 244b and the sidewall of the mixing chamber 212b. First and second injection fluids are deflected to flow in a substantially radial direction by the deflection members 242b, 244b in opposite directions and forced to flow through the radial space 246b. The rapid change in the flow direction promotes turbulent mixing of the first injection fluid and the second injection fluid within the mixing chamber 212b once the first and second injection fluids are recombined downstream of the deflection members 242b, 244b.

Figure 9:
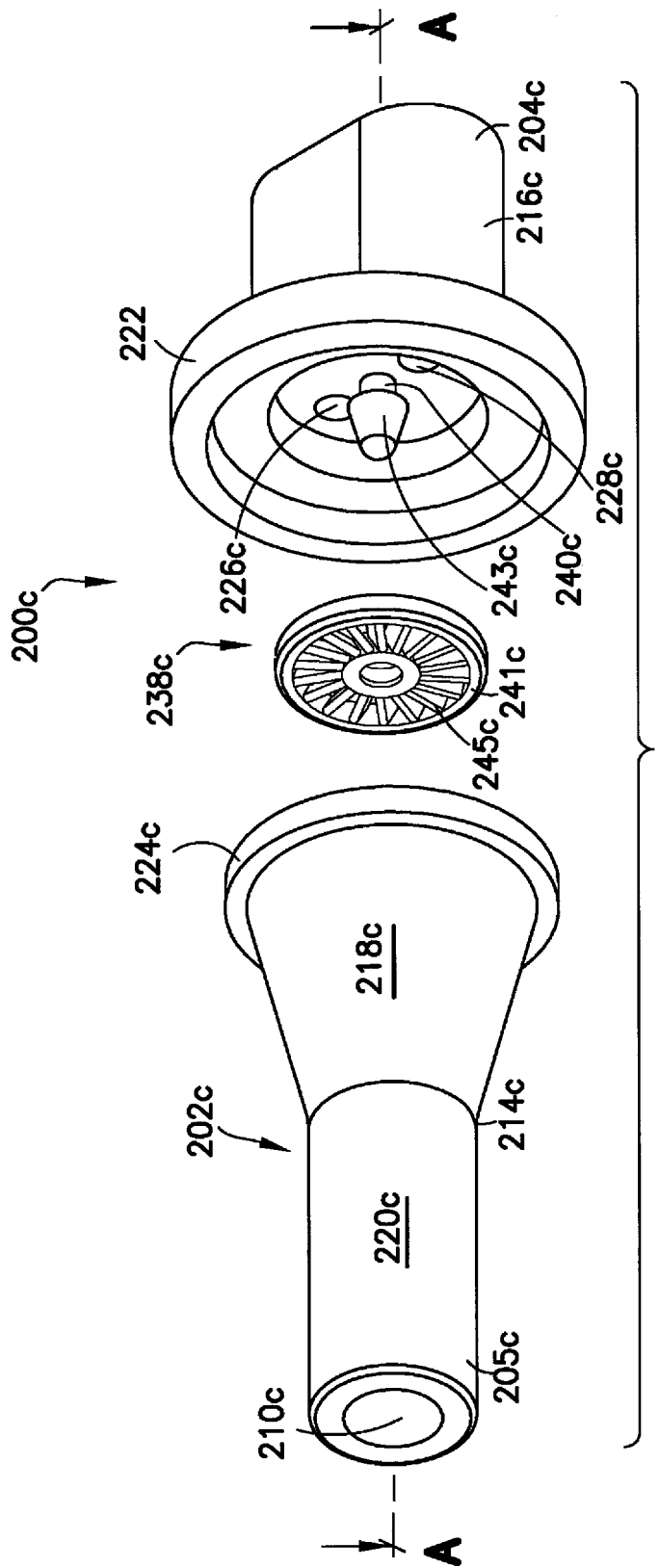
FIG. 9 is an exploded perspective view of the flow mixing device in accordance with a third embodiment.
Figure 10:
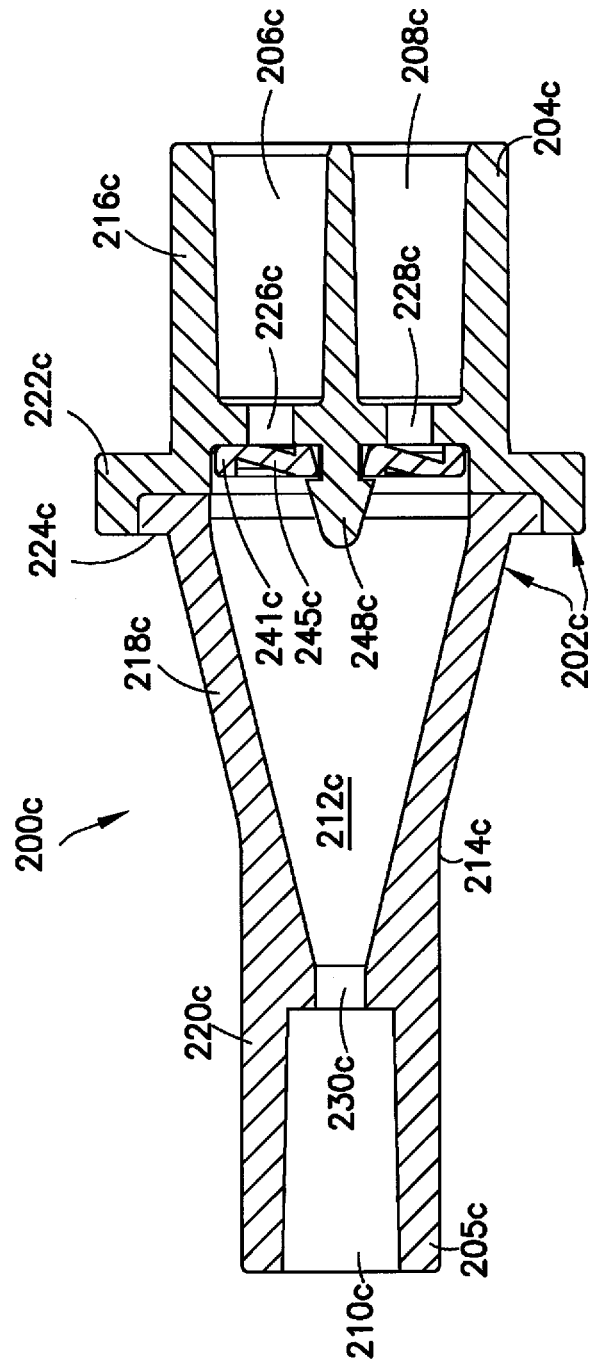
FIG. 10 is a cross-sectional view of an assembled flow mixing device taken along line A-A shown in FIG. 9.

With reference to FIGS. 9-10, a flow mixing device 200c is illustrated in accordance with a third embodiment. Flow mixing device 200c includes a housing 202c having a proximal end 204c opposite a distal end 205c. The proximal end 204c of the housing 202c includes a first fluid port and a second fluid port which are connected or connectable to respective first fluid line 116 and second fluid line 118. The proximal end 204c of the housing 202c may include a connector (not shown) for connecting the first and second fluid lines 116, 118 to the flow mixing device 200c. The distal end 205c of the housing 202c includes a third fluid port 210c which is connected or connectable to the third fluid line 120 (not shown in FIGS. 9-10). The distal end 205c of the housing 202c may include a connector (not shown) for connecting the flow mixing device 200c to the third fluid line 120 or to a catheter.

With reference to FIG. 10, the housing 202c of the flow mixing device 200c includes a first portion 214c and second portion 216c. The first portion 214c of the housing 202c has a substantially conical proximal end 218c and a substantially cylindrical distal end 220c. A collar 222c surrounds the base of the first portion 214c. The second portion 216c includes a flange 224c that corresponds to the collar 222c of the first portion 214c to receive the flange 224c within the collar 222c. In another embodiment, the collar 222c is provided on the second portion 216c, while the flange 224c is provided on the first portion 214c of the housing 202c. In one preferred and non-limiting embodiment, the first and second portions 214c, 216c are permanently coupled together by gluing, ultrasonic welding, an interference fit connection, or other mechanical securing arrangement.

The housing 202c of the flow mixing device 200c defines a mixing chamber 212c (shown in FIG. 10) where first and second injection fluids mix to form a mixed solution. The mixing chamber 212c is adapted for providing a homogenous mixing flow under turbulent conditions to promote a thorough mixing of the first and second injection fluids to produce a substantially homogeneous mixed solution.

With continuing reference to FIG. 10, the first and second fluid ports 206c, 208c extend through the second portion 216c and are in fluid communication with the mixing chamber 212c through first and second fluid orifices 226c, 228c, respectively. First and second fluid ports 206c, 208c are substantially parallel to each other. In other embodiments, first and second fluid ports 206c, 208c may be angled relative a longitudinal axis of flow mixing device 200c such that fluid flow of the first and second injection fluids converges or diverges relative to the longitudinal axis. In one exemplary embodiment, a contrast medium may be supplied through the first fluid port 206c and saline may be injected through the second fluid port 208c. Fluid flowing through the first and second fluid ports 206c, 208c passes through the first and second fluid orifice 226c, 228c having a reduced cross-section relative to the first and second fluid ports 206c, 208c. First and second fluid orifices 226c, 228c have equal diameters. In another embodiment, the diameter of the first fluid orifice 226c may be larger or smaller relative to the diameter of the second fluid orifice 228c. First and second injection fluids mix within the mixing chamber 212c to form a mixed solution. The mixed solution is discharged from the mixing chamber 212c through a third fluid orifice 230c provided at a distal end of the first portion 214c of the housing 202c. The third fluid orifice 230c is in fluid communication with a third fluid port 230c that discharges the mixed fluid from the mixing device 200c through the fluid conduit (not shown).

As best shown in FIG. 10, the mixing chamber 212c is defined within the interior of the first portion 214c. The mixing chamber 212c has a generally conical shape that narrows from the proximal end 218c to the distal end 220c, such that a cross-sectional shape of the mixing chamber 212c is substantially circular. Alternatively, the cross-sectional shape of the mixing chamber 212c may be an ellipse or any other shape formed from a curved line. In another embodiment, the mixing chamber 212c may have a first portion that narrows from the proximal end 218c to the distal end 220c and a substantially cylindrical portion that extends therefrom.

The second portion 216c includes a fluid flow dispersion device 238c having a central hub 240c and a turbine wheel 241c rotatable around the central hub 240c, as shown more fully in FIG. 9. The central hub 240c is located between the first and second fluid orifices 226c, 228c and extends in a longitudinal direction toward the distal end 220c of the first portion 214c. Turbine wheel 241c is rotatably disposed on the central hub 240c and is retained in a longitudinal direction by a cap 243c. Turbine wheel 241c includes a plurality of rotor blades 245c extending radially outward from a central portion of the turbine wheel 241c. Each rotor blade 245c is angled with respect to a longitudinal axis of the mixing chamber 212c such that first and second injection fluids exiting from first and second fluid orifices 226c, 228c are deflected in a radial direction. Fluid exiting from the first and second fluid orifices 226c, 228c strikes the rotor blades 245c and causes the turbine wheel 241c to rotate. Rotation of the turbine wheel 241c causes a scattering of the first and second fluids within the mixing chamber 212c to promote a homogenous mixing of the fluids.

Figure 11:
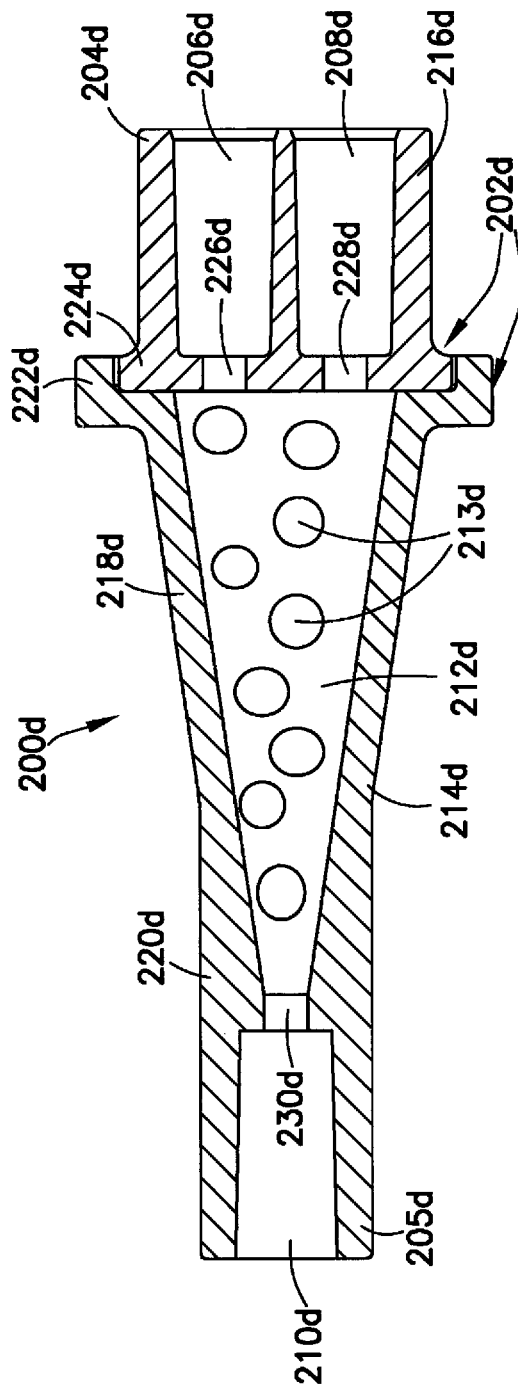
FIG. 11 is a cross-sectional view of a flow mixing device in accordance with a fourth embodiment.

With reference to FIG. 11, a flow mixing device 200d is illustrated in accordance with a fourth embodiment. The housing 202d of the flow mixing device 200d is substantially similar to the housing 202a of the flow mixing device 200a described above. Reference numerals 200d-230d in FIG. 11 are used to illustrate identical components as reference numerals 200a-230a in FIGS. 4-5. As the previous discussion regarding the flow mixing device 200a generally shown in FIGS. 4-6C is applicable to the embodiment shown in FIG. 11, only the relevant differences between these systems are discussed hereinafter.

With reference to FIG. 11, the mixing chamber 212d is defined within the interior of the first portion 214d. The mixing chamber 212d has a generally cylindrical shape having a substantially circular cross-section. Alternatively, the cross-sectional shape of the mixing chamber 212d may be an ellipse or any other shape formed from a curved line. In another embodiment, the mixing chamber 212d may have a first portion that narrows from the proximal end 218d to the distal end 220d to define a conical profile.

The mixing chamber 212d has a plurality of mixing balls 213d disposed within. Each mixing ball 213d is substantially spherical and has a diameter that is larger than the diameter of the smallest of the first, second, and third fluid orifices 226d, 228d, 230d, respectively, in order to eliminate blocking of the fluid ports. Desirably, each of the plurality of mixing balls 213d has a diameter sufficiently large to avoid complete occlusion of the first, second, and third fluid orifices 226d, 228d, 230d. As the first and second injection fluids enter the mixing chamber 212d, the mixing balls 213d are agitated by the fluid flow and move about the mixing chamber 212d. In an embodiment where the housing 202d is transparent, the mixing balls 213d provide a visual indication of injection and mixing. In a purge cycle, the position of the mixing balls 213d within the mixing chamber 212d is indicative of whether the purge is completed. In a further embodiment, the mixing balls 213d may provide an audible indication of injection as the mixing balls 213d bounce off of the walls of the mixing chamber 212d and produce noise.

Figure 12:
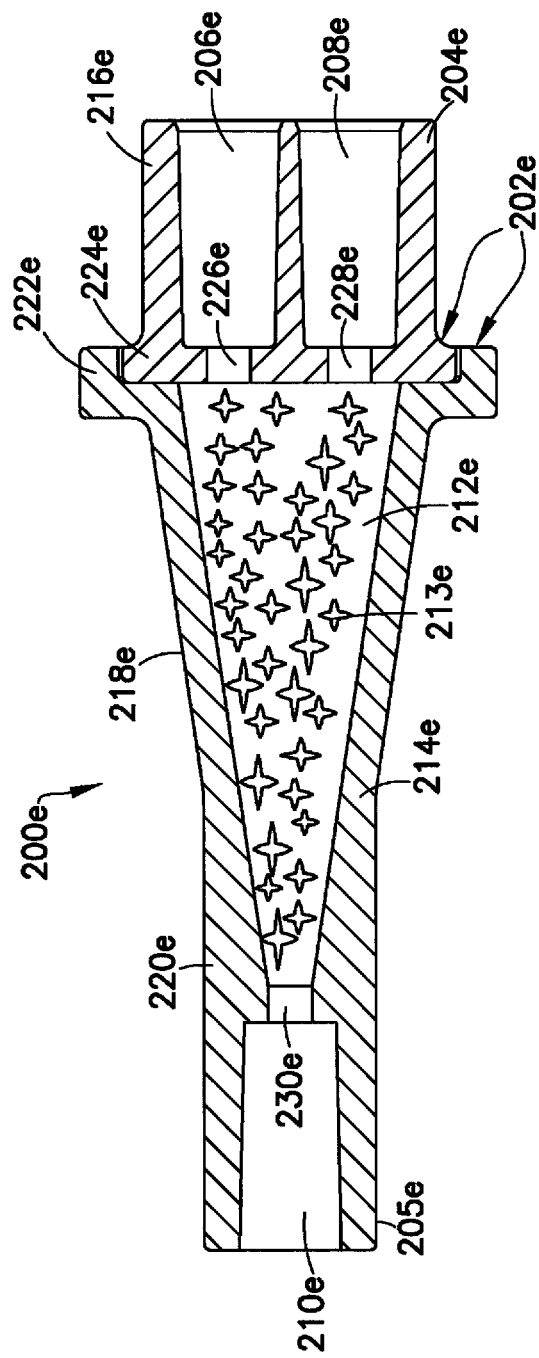
FIG. 12 is a cross-sectional view of a flow mixing device in accordance with a fifth embodiment.

With reference to FIG. 12, a flow mixing device 200e is illustrated in accordance with a fifth embodiment. The flow mixing device 200e is substantially similar to the flow mixing device 200d described above. Reference numerals 200e-230e in FIG. 12 are used to illustrate identical components as reference numerals 200d-230d in FIG. 11. As the previous discussion regarding the flow mixing device 200d is applicable to the embodiment shown in FIG. 11, only the relevant differences between these systems are discussed hereinafter.

Whereas the flow mixing device 200d includes a plurality of mixing balls 213d disposed within the mixing chamber 212d, the flow mixing device 200e includes a porous filter material filing at least a portion of the mixing chamber 212e. In particular, an open-cell filter element 213e fills the mixing chamber 212e and creates a fluid path restriction which forces the first and second injection fluids to mix while passing through the pores. In one embodiment, the filter element 213e is provided only on one lateral side of the mixing chamber 212e in order to increase a pressure drop of one of the first or second injection fluids.

Figure 13:
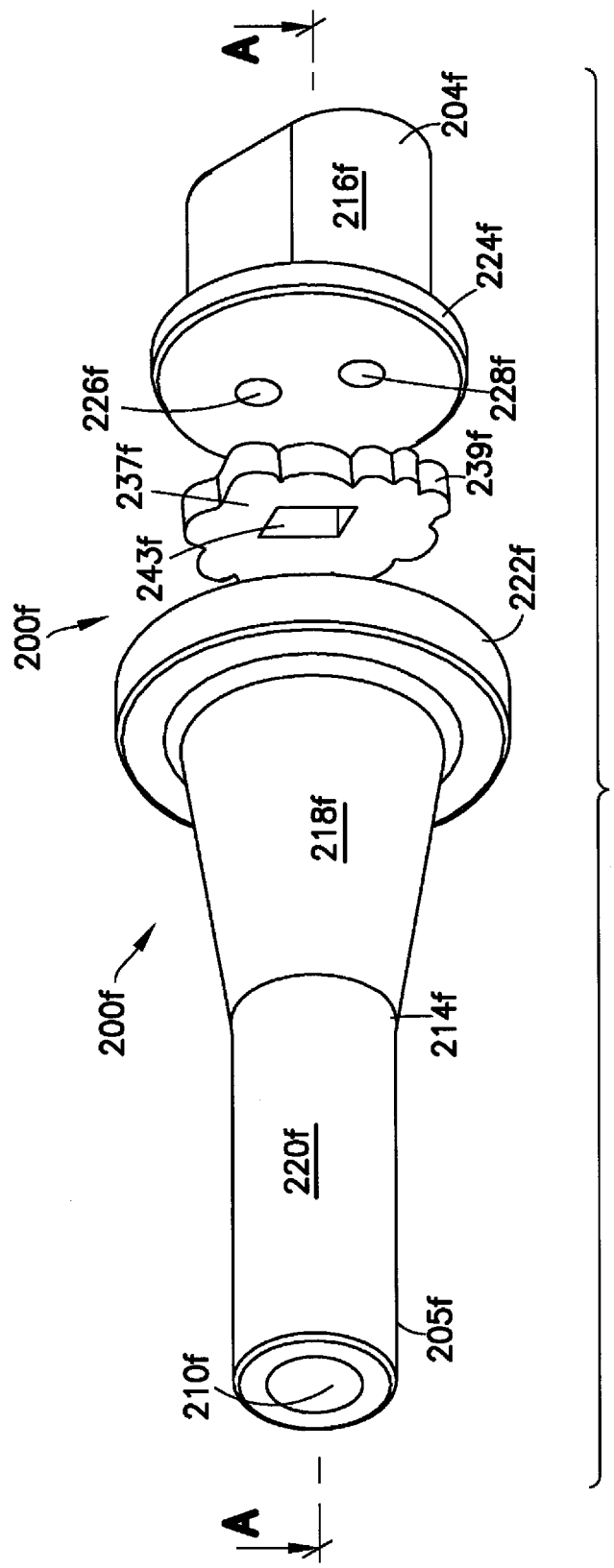
FIG. 13 is an exploded perspective view of a flow mixing device in accordance with a sixth embodiment.

With reference to FIG. 13, a flow mixing device 200f is illustrated in accordance with a sixth embodiment. Flow mixing device 200f includes a housing 202f having a proximal end 204f opposite a distal end 205f. The proximal end 204f of the housing 202f includes a first fluid port 206f and a second fluid port 208f which are connected or connectable to respective first fluid line 116 and second fluid line 118. The proximal end 204f of the housing 202f may include a connector (not shown) for connecting the first and second fluid lines 116, 118 to the flow mixing device 200f. The distal end 205f of the housing 202f includes a third fluid port 210f which is connected or connectable to the third fluid line 120. The distal end 205f of the housing 202f may include a connector (not shown) for connecting the flow mixing device 200f to the third fluid line 120 or to a catheter.

The housing 202f of the flow mixing device 200f defines a mixing chamber 212f (shown in FIG. 14) where first and second injection fluids mix to form a mixed solution. The mixing chamber 212f is adapted for providing a homogenous mixing flow under turbulent conditions to promote a thorough mixing of the first and second injection fluids to produce a substantially homogeneous mixed solution. Additionally, the mixing chamber 212f is also adapted to eliminate zones of stagnant fluid flow. The housing 202f is desirably formed from a medical-grade plastic material having sufficient rigidity to prevent any substantial expansion of the housing 202f during the injection procedure. For example, the housing 202f is adapted to retain its shape without appreciable expansion at an injection pressure of 1200 psi.

Figure 14:
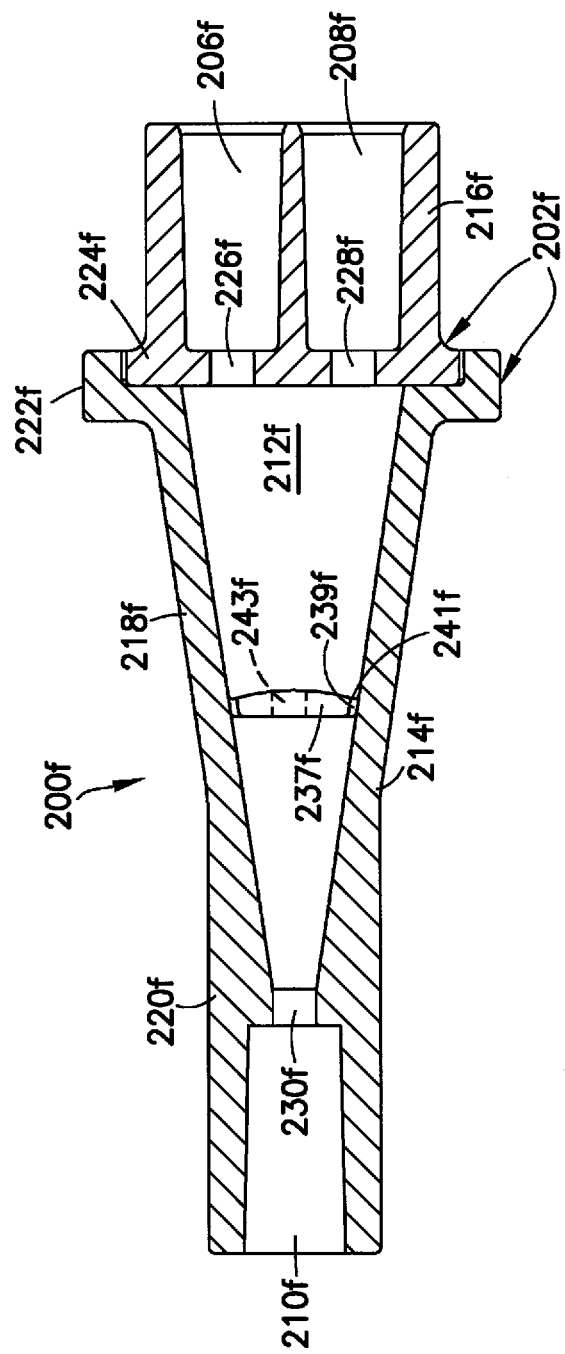
FIG. 14 is a cross-sectional view of an assembled flow mixing device taken along line A-A shown in FIG. 13.
Figure 15:
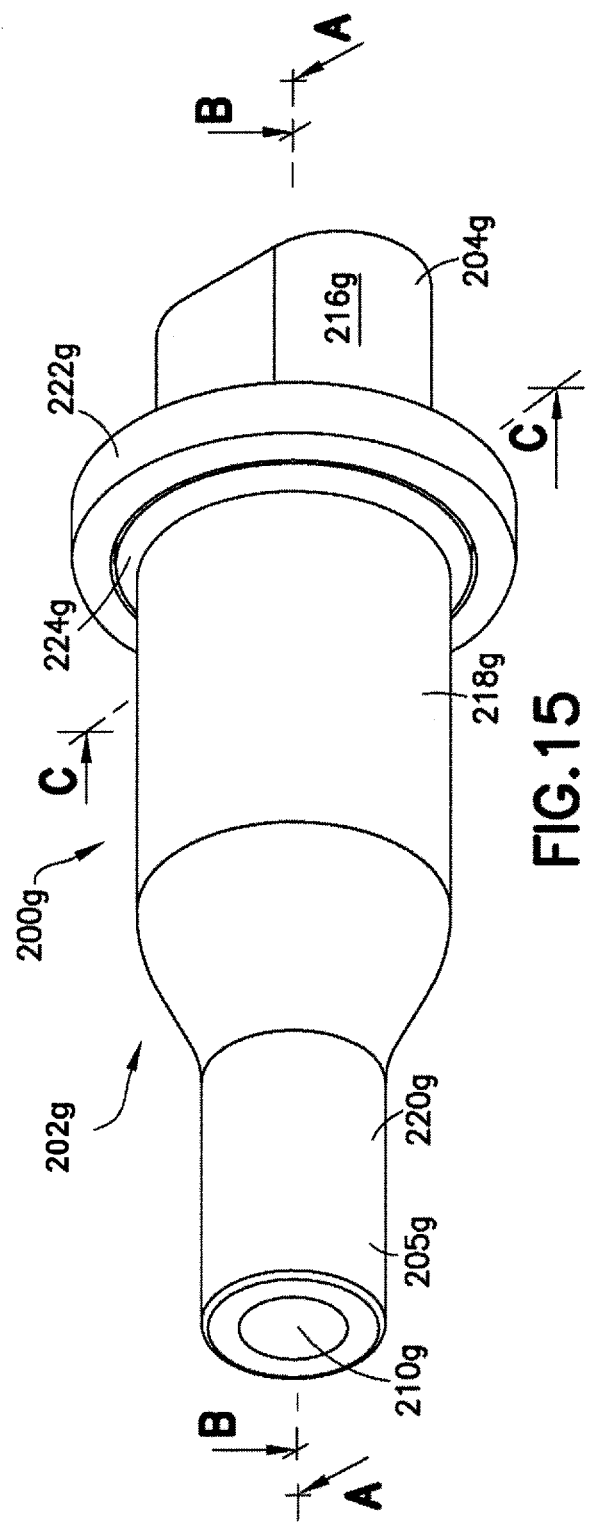
FIG. 15 is a top perspective view of a flow mixing device in accordance with a seventh embodiment.

With reference to FIG. 14, the second portion 216f includes a first fluid port 206f for receiving a first injection fluid through a first fluid conduit (not shown) and a second fluid port 208f for receiving a second injection fluid through a second fluid conduit (not shown). First and second fluid ports 206f, 208f extend through the second portion 216f and are in fluid communication with the mixing chamber 212f through first and second fluid orifices 226f, 228f, respectively. First and second fluid ports 206f, 208f are substantially parallel to each other. In other embodiments, first and second fluid ports 206f, 208f may be angled relative to a longitudinal axis of flow mixing device 200f such that fluid flow of the first and second injection fluids converges or diverges relative to the longitudinal axis. In one exemplary embodiment, a contrast medium may be supplied through the first fluid port 206f and saline may be injected through the second fluid port 208f. Fluid flowing through the first and second fluid ports 206f, 208f passes through the first and second fluid orifices 226f, 228f having a reduced cross-section relative to the first and second fluid ports 206f, 208f. First and second fluid orifices 226f, 228f have equal diameters. In another embodiment, the diameter of the first fluid orifice 226f may be larger or smaller relative to the diameter of the second fluid orifice 228f. First and second injection fluids mix within the mixing chamber 212f to form a mixed solution. The mixed solution is discharged from the mixing chamber 212f through a third fluid orifice 230f provided at a distal end of the first portion 214f of the housing 202f. The third fluid orifice 230f is in fluid communication with the third fluid port 210f that discharges the mixed fluid from the mixing device 200f through a fluid conduit (not shown).

The mixing chamber 212f is defined within the interior of the first portion 214f. The mixing chamber 212f has a generally conical shape having a substantially circular cross-section. Alternatively, the cross-sectional shape of the mixing chamber 212f may be an ellipse or any other shape formed from a curved line.

As best shown in FIG. 13, a disc 237f is provided between the first portion 214f and the second portion 216f. The disc 237f is disposed inside the mixing chamber 212f between the proximal end 218f and the distal end 220f of the first portion 214f. The disc 237f has a generally circular shape adapted to fit inside the mixing chamber 212f. Desirably, the disc 237f is adapted to be fixed inside the mixing chamber 212f and extend substantially perpendicular to a longitudinal axis of the mixing chamber 212f. The disc 237f includes a plurality of recesses 239f extending radially inward from the outer circumference of the disc 237f. When positioned inside the mixing chamber 212f, the recesses 239f define a fluid passage 241f through which mixed solution can pass. Additionally, the disc 237f includes a central opening 243f extending through the thickness of the disc 237f. As is well known from the fundamental principles of fluid dynamics, a velocity profile of a fluid traveling through a circular conduit has a maximum velocity value at the center of the conduit and a minimum velocity value at the sidewall of the conduit. A stagnation point exists at the surface of the conduit, where the fluid is brought to rest by the conduit and its local velocity is zero. In order to modify the velocity profile of the first and second injection fluids such that they mix inside the mixing chamber 212f to create a mixed solution, disc 237f restricts the fluid such that the fluid flow closest to the sidewall of the mixing chamber 212f is less restricted than the fluid flow closer to the center of the mixing chamber 212f. The fluid passages 241f provided around the perimeter of the disc 237f do not cause a restriction in the fluid where fluid flow is at its lowest value, while the body of the disc 237f acts as a barrier to reduce the velocity profile of the fastest moving fluid. The central opening 243f prevents an excess buildup of backup pressure by allowing fluid to pass therethrough. The fluid obstruction caused by the disc 237f causes a turbulent flow downstream of the disc 237f to promote homogeneous mixing of the first and second injection fluids.

With reference to FIGS. 15-17C, a flow mixing device 200g is illustrated in accordance with a seventh embodiment. Flow mixing device 200g includes a housing 202g having a proximal end 204g opposite a distal end 205g. The proximal end 204g of the housing 202g includes a first fluid port 206g and a second fluid port 208g (shown in FIG. 17B) which are connected or connectable to respective first fluid line 116 and second fluid line 118. The proximal end 204g of the housing 202g may include a connector (not shown) for connecting the first and second fluid lines 116, 118 to the flow mixing device 200g. The distal end 205g of the housing 202g includes a third fluid port 210g which is connected or connectable to the third fluid line 120. The distal end 205g of the housing 202g may include a connector (not shown) for connecting the flow mixing device 200g to the third fluid line 120 or to a catheter.

The housing 202g of the flow mixing device 200g defines a mixing chamber 212g (shown in FIG. 17B) where first and second injection fluids mix to form a mixed solution. The mixing chamber 212g is adapted for providing a homogenous mixing flow under turbulent conditions to promote a thorough mixing of the first and second injection fluids to produce a substantially homogeneous mixed solution. Additionally, the mixing chamber 212g is also adapted to eliminate zones of stagnant fluid flow. The housing 202g is desirably formed from a medical-grade plastic material having sufficient rigidity to prevent any substantial expansion of the housing 202g during the injection procedure. For example, the housing 202g is adapted to retain its shape without appreciable expansion at an injection pressure of 1200 psi.

With specific reference to FIGS. 17A-17C, the second portion 216g includes a first fluid port 206g for receiving a first injection fluid through a first fluid conduit (not shown) and a second fluid port 208g for receiving a second injection fluid through a second fluid conduit (not shown). First and second fluid ports 206g, 208g extend through the second portion 216g and are in fluid communication with the mixing chamber 212g through first and second fluid orifices 226g, 228g, respectively. First and second fluid ports 206g, 208g are substantially parallel to each other. In other embodiments, first and second fluid ports 206g, 208g may be angled relative a longitudinal axis of flow mixing device 200g such that fluid flow of the first and second injection fluids converges or diverges relative to the longitudinal axis. In one exemplary embodiment, a contrast medium may be supplied through the first fluid port 206g and saline may be injected through the second fluid port 208g. Fluid flowing through the first and second fluid ports 206g, 208g passes through the first and second fluid orifice 226g, 228g having a reduced cross-section relative to the first and second fluid ports 206g, 208g. First and second fluid orifices 226g, 228g have approximately equal diameters. In another embodiment, the diameter of the first fluid orifice 226g may be larger or smaller relative to the diameter of the second fluid orifice 228g. First and second injection fluids mix within the mixing chamber 212g to form a mixed solution. The mixed solution is discharged from the mixing chamber 212g through a third fluid orifice 230g provided at a distal end of the first portion 214g of the housing 202g. The third fluid orifice 230g is in fluid communication with the third fluid port 210g that discharges the mixed fluid from the mixing device 200g through a fluid conduit (not shown).

The mixing chamber 212g is defined within the interior of the first portion 214g. The mixing chamber 212g has a generally cylindrical shape having a substantially circular cross-section. Alternatively, the cross-sectional shape of the mixing chamber 212g may be an ellipse or any other shape formed from a curved line. The mixing chamber 212g may have a first portion that narrows from the proximal end 218g to the distal end 220g to define a conical profile.

With continuing reference to FIGS. 17A-17C, and referring back to FIG. 16, flow mixing device 200g includes a flow dispersion insert 237g disposed between the first portion 214g and the second portion 216g. The flow dispersion insert 237g is adapted for being received within a cavity of the first portion 214g. The flow dispersion insert 237g has a substantially tubular structure with two pins 239g extending longitudinally outward from a distal end of a sidewall of the flow dispersion insert 237g. Each of the pins 239g is received in a corresponding pin hole 241g provided on a stop surface 243g at a distal end of the cavity of the first portion 214g. Pins 239g are adapted for engaging the pin holes 241g to prevent rotation of flow dispersion insert 237g relative to first portion 214g of the housing 202g. As best shown in FIG. 17A, the flow dispersion insert 237g includes a hydrofoil element 245g extending across a central portion of the interior of the tubular structure of the flow dispersion insert 237g. The hydrofoil element 245g includes a leading edge 247g located at the proximate end and a trailing edge 249g at the distal end of the flow dispersion insert 237g. The hydrofoil element 245g further includes an upper chord 251g extending between the leading edge 247d and the trailing edge 249g, and a lower chord 253g extending between the leading edge 247g and the trailing edge 249g opposite the upper chord 251g. Upper and lower chords 251g, 253g define the cross-sectional profile of the hydrofoil element 245g and define the flow characteristics of the fluid passing across the hydrofoil element 245g. As is well known from hydrodynamics principles, a convex profile of the upper chord 251g will cause a fluid stream to accelerate over the upper surface of the hydrofoil element 245g, thereby creating a condition of low fluid pressure. On the other hand, a flat or concave profile of the lower chord 253g will cause a fluid stream to decelerate over the lower surface of the hydrofoil element 245g, thereby creating a condition of high fluid pressure. As fluid traveling across the upper chord 251g joins the fluid traveling across the lower chord 253g at the trailing edge 249g, vortices shed off of the trailing edge 249g result in turbulent fluid flow distally of the trailing edge 249g to promote a homogeneous mixing of the first and second injection fluids inside the mixing chamber 212g. In the embodiment shown in FIG. 17B, first and second fluid orifices 226g, 228g are substantially parallel to the leading edge 247g of the hydrofoil element 245g. In another embodiment, first and second fluid orifices 226g, 228g may be oriented perpendicularly relative to the leading edge 247g of the hydrofoil element 245g.

Figure 18A:
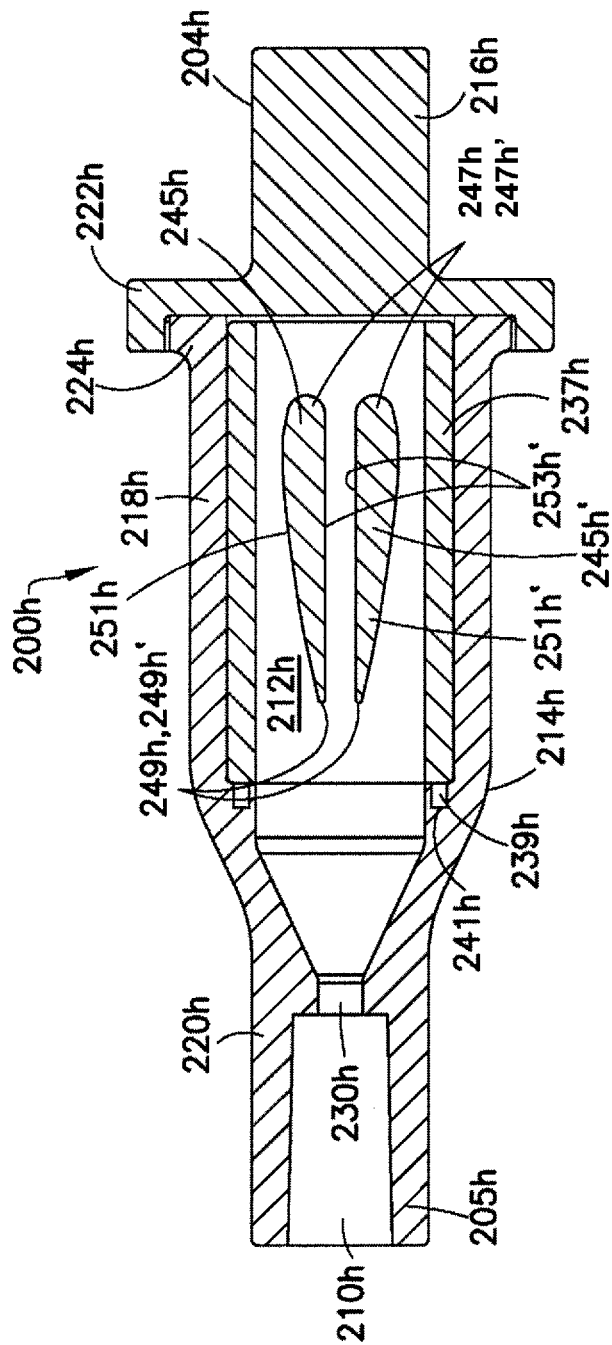
FIG. 18A is a cross-sectional view of a flow mixing device in accordance with an eighth embodiment.

With reference to FIGS. 18A-18C, a flow mixing device 200h is illustrated in accordance with an eighth embodiment. The flow mixing device 200h is substantially similar to the flow mixing device 200g described above. Reference numerals 200h-230h in FIGS. 18A-18C are used to illustrate identical components as reference numerals 200g-230g in FIGS. 15-17C. Whereas the flow mixing device 200g includes only one hydrofoil element 245g, the flow mixing device 200h includes a plurality of hydrofoils. In particular, with reference to FIGS. 18A-18C, flow mixing device 200h includes a flow dispersion insert 237h disposed between the first portion 214h and the second portion 216h. The flow dispersion insert 237h is adapted for being received within a cavity of the first portion 214h. The flow dispersion insert 237h has a substantially tubular structure with two pins 239h extending longitudinally outward from a distal end of a sidewall of the flow dispersion insert 237h. Each of the pins 239h is received in a corresponding pin hole 241h provided on a stop surface 243h at a distal end of the cavity of the first portion 214h. Pins 239h are adapted for engaging the pin holes 241h to prevent rotation of flow dispersion insert 237h relative to first portion 214h of the housing 202h. As best shown in FIG. 18A, the flow dispersion insert 237h includes two hydrofoil elements 245h, 245h' extending across a central portion of the interior of the tubular structure of the flow dispersion insert 237h. The hydrofoil elements 245h, 245h' are offset from each other such that fluid may pass therebetween. The hydrofoil elements 245h, 245h' include a leading edge 247h, 247h' located at the proximate end and a trailing edge 249h, 249h' at the distal end of the flow dispersion insert 237h. The hydrofoil elements 245h, 245h' further include an upper chord 251h, 251h' extending between the leading edge 247h, 247h' and the trailing edge 249h, 249h', and a lower chord 253h, 253h' extending between the leading edge 247h, 247h' and the trailing edge 249h, 249h' opposite the upper chord 251h, 251h'. Upper cords 251h, 251h' and lower chords 253h, 253h' define the cross-sectional profile of the hydrofoil elements 245h, 245h' and define the flow characteristics of the fluid passing across the hydrofoil elements 245h, 245h'. Hydrofoil elements 245h, 245h' may be arranged such that (a) the leading edge 247h of the first hydrofoil element 245h is aligned substantially parallel with the leading edge 247h' of the second hydrofoil element 245h', (b) the upper chord 251h of the first hydrofoil element 245h is adjacent to the upper chord 251h' of the second hydrofoil element 245h', (c) the lower chord 253h of the first hydrofoil element 245h is adjacent to the lower chord 253h' of the second hydrofoil element 245h', or (d) the upper chord 251h of the first hydrofoil element is adjacent to the lower chord 253h' of the second hydrofoil element 245h'. As is well known from hydrodynamics principles, a convex profile of the upper chord 251h, 251h' will cause a fluid stream to accelerate over the upper surface of the hydrofoil element 245h, 245h', thereby creating a condition of low fluid pressure. On the other hand, a flat or concave profile of the lower chord 253h, 253h' will cause a fluid stream to decelerate over the lower surface of the hydrofoil element 245h, 245h', thereby creating a condition of high fluid pressure. As fluid traveling across the upper chord 251h, 251h' joins the fluid traveling across the lower chord 253h, 253h' at the trailing edge 249h, 249h', vortices shed off of the trailing edge 249h, 249h' result in turbulent fluid flow distally of the trailing edge 249h, 249h' to promote a homogeneous mixing of the first and second injection fluids inside the mixing chamber 212h. In the embodiment shown in FIG. 18B, first and second fluid orifices 226h, 228h are substantially parallel to the leading edges 247h, 247h' of the two hydrofoil elements 245h, 245h'. In another embodiment, first and second fluid orifices 226h, 228h may be oriented perpendicularly relative to the leading edges 247h, 246h' of the two hydrofoil elements 245h, 245h'.

With reference to FIGS. 19-20B, a flow mixing device 200i is illustrated in accordance with a ninth embodiment. Flow mixing device 200i includes a housing 202i having a proximal end 204i opposite a distal end 205i. The proximal end 204i of the housing 202i includes a first fluid port 206i and a second fluid port 208i (shown in FIG. 20A) which are connected or connectable to respective first fluid line 116 and second fluid line 118. The proximal end 204i of the housing 202i may include a connector (not shown) for connecting the first and second fluid lines 116, 118 to the flow mixing device 200i. The distal end 205i of the housing 202i includes a third fluid port 210i which is connected or connectable to the third fluid line 120. The distal end 205i of the housing 202i may include a connector (not shown) for connecting the flow mixing device 200i to the third fluid line 120 or to a catheter.

The housing 202i of the flow mixing device 200i defines a mixing chamber 212i (shown in FIG. 20A) where first and second injection fluids mix to form a mixed solution. The mixing chamber 212i is adapted for providing a homogenous mixing flow under turbulent conditions to promote a thorough mixing of the first and second injection fluids to produce a substantially homogeneous mixed solution. Additionally, the mixing chamber 212i is also adapted to eliminate zones of stagnant fluid flow. The housing 202i is desirably formed from a medical-grade plastic material having sufficient rigidity to prevent any substantial expansion of the housing 202i during the injection procedure. For example, the housing 202i is adapted to retain its shape without appreciable expansion at an injection pressure of 1200 psi.

With specific reference to FIGS. 20A-20B, the first and second fluid ports 206i, 208i extend through the second portion 216i and are in fluid communication with the mixing chamber 212i through first and second fluid orifices 226i, 228i, respectively. First and second fluid ports 206i, 208i are substantially parallel to each other. In other embodiments, first and second fluid ports 206i, 208i may be angled relative a longitudinal axis of flow mixing device 200i such that fluid flow of the first and second injection fluids converges or diverges relative to the longitudinal axis. In one exemplary embodiment, a contrast medium may be supplied through the first fluid port 206i and saline may be injected through the second fluid port 208i. Fluid flowing through the first and second fluid ports 206i, 208i passes through the first and second fluid orifice 226i, 228i having a reduced cross-section relative to the first and second fluid ports 206i, 208i. First and second fluid orifices 226i, 228i have equal diameters. In another embodiment, the diameter of the first fluid orifice 226i may be larger or smaller relative to the diameter of the second fluid orifice 228i. First and second injection fluids mix within the mixing chamber 212i to form a mixed solution. The mixed solution is discharged from the mixing chamber 212i through a third fluid orifice 230i provided at a distal end of the first portion 214i of the housing 202i. The third fluid orifice 230i is in fluid communication with the third fluid port 210i that discharges the mixed fluid from the mixing device 200i through a fluid conduit, such as the third fluid line 120 connected to a catheter, as discussed above with reference to FIG. 3.

With reference to FIGS. 19 and 20A, flow mixing device 200i includes a plurality of flow dispersion inserts 237i disposed between the first portion 214i and the second portion 216i. The flow dispersion inserts 237i are adapted for being received within a cavity of the first portion 214i. The flow dispersion inserts 237i have a substantially tubular structure with two pins 239h extending longitudinally outward from a distal end of a sidewall of the flow dispersion insert 237i and two pin holes 241i extending into the sidewall of the flow dispersion insert at the proximal end thereof. Each of the pins 239i is received in the corresponding pin hole 241i provided on the adjacent flow dispersion insert 237i. The pins 239i of the flow dispersion insert closest to the distal end of the first portion 214i is received inside a stop surface 243i at a distal end of the first portion 214i. Pins 239i are adapted for engaging the pin holes 241i to prevent rotation of flow dispersion insert 237i relative to first portion 214i of the housing 202i.

With continuing reference to FIG. 20A, each flow dispersion insert 237i has a substantially cylindrical exterior adapted to be received inside the first portion 214i. Each flow dispersion insert 237i further includes a hollow interior. Collectively, the hollow interiors of the plurality of flow dispersion inserts 237i define the mixing chamber 212i. Each flow dispersion insert includes a plurality of wings 245i that extend radially inward from the inside sidewall of the flow dispersion insert 237i. The wings 245i are spaced apart at equal intervals about the inner circumference of the flow dispersion insert 237i. For example, the embodiment illustrated in FIG. 20A includes four wings 245i spaced apart at 90° intervals. Adjacent flow dispersion inserts 237i are desirably rotated with respect to each other such that wings 245i of one flow dispersion insert 237i are angularly offset with regard to the adjacent flow dispersion insert 237i. In the embodiment shown in FIG. 20A, the three flow dispersion inserts 237i are provided, where the first and last flow dispersion inserts 237i are positioned such that the wings 245i on these inserts are in angular alignment with respect to the longitudinal axis extending through the mixing chamber 212i. The middle flow dispersion insert 237i is angularly offset with regard to the first and last flow dispersion inserts 237i such that the wings 245i on the middle insert are offset with regard to the first and last flow dispersion inserts 237i. While FIG. 20A illustrates three flow dispersion inserts 237i, one of ordinary skill in the art would appreciate that any number of flow dispersion inserts 237i can be provided. The wings 245i in each flow dispersion insert 237i create an obstruction in the fluid path through the mixing chamber 212i to generate a turbulent fluid flow through the mixing chamber 212i.

Figure 21:
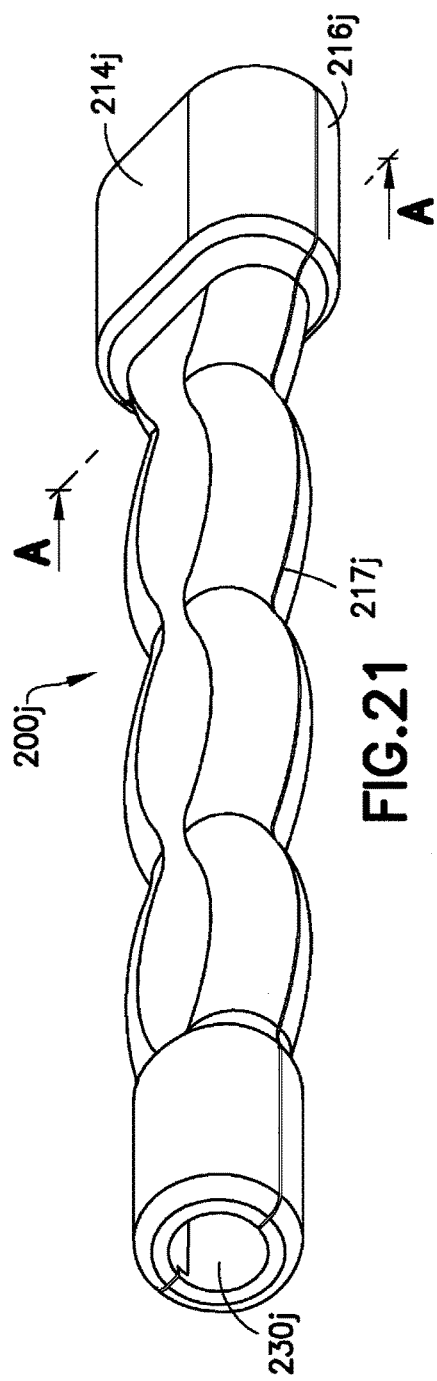
FIG. 21 is a top perspective view of a flow mixing device in accordance with a tenth embodiment.
Figure 23:
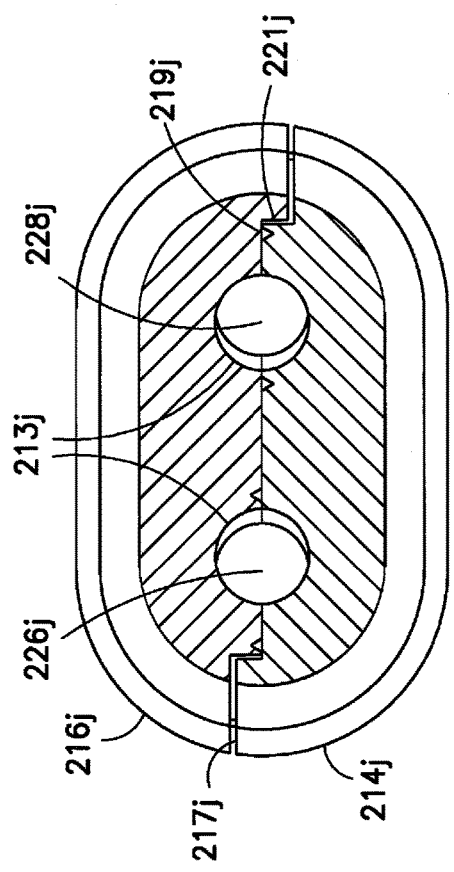
FIG. 23 is a cross-sectional view of an assembled flow mixing device taken along line A-A shown in FIG. 21.
Figure 22:
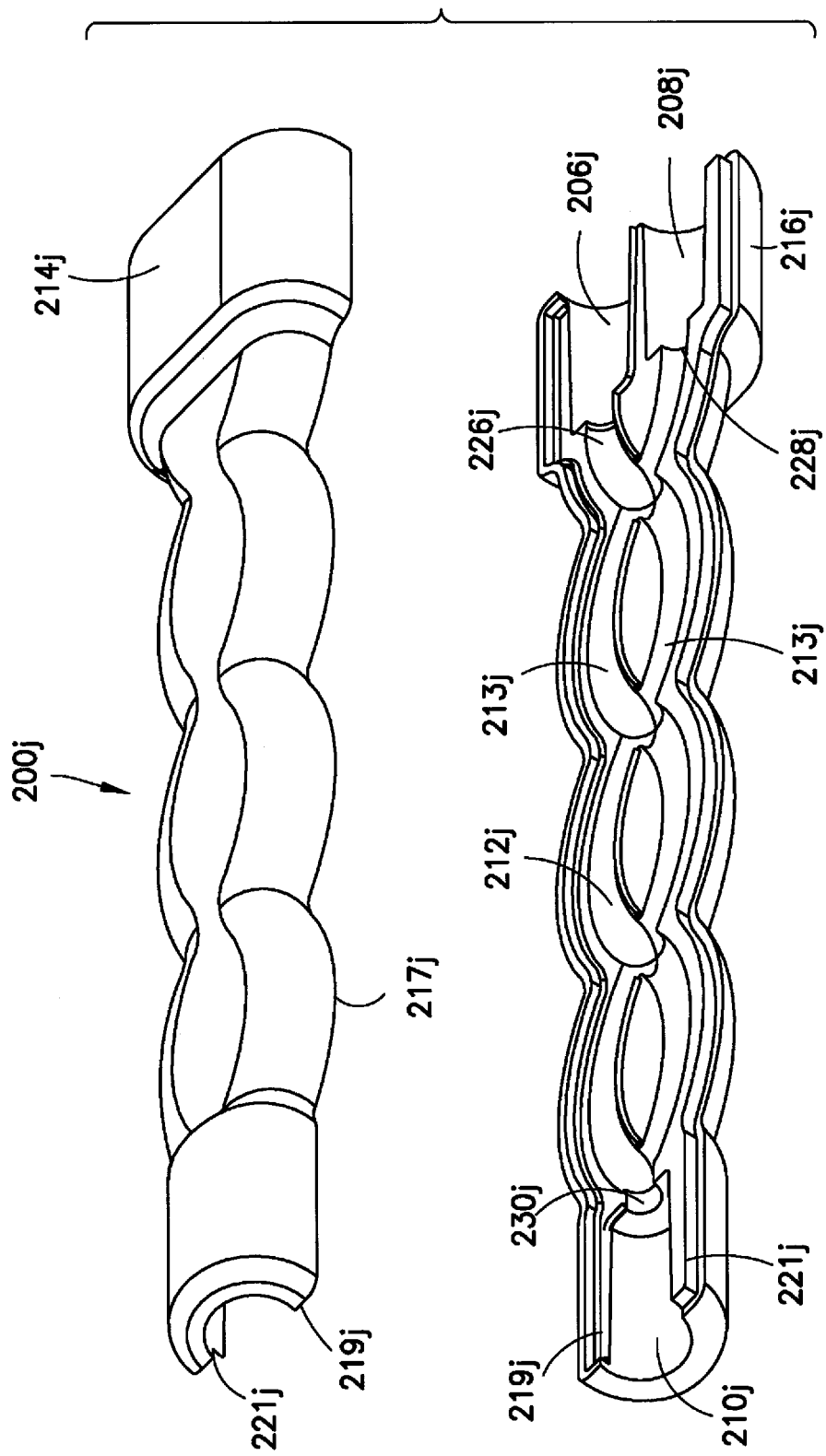
FIG. 22 is an exploded perspective view of the flow mixing device shown in FIG. 21.

With reference to FIGS. 21-23, a flow mixing device 200j is illustrated in accordance with a tenth embodiment. Flow mixing device 200j includes a housing 202j having a proximal end 204j opposite a distal end 205j. The distal end 205j of the housing 202j may include a connector (not shown) for connecting the flow mixing device 200j to the third fluid line 120 or to a catheter. The housing 202j of the flow mixing device 200j defines a mixing chamber 212j (shown in FIG. 22) where first and second injection fluids mix to form a mixed solution. The mixing chamber 212j is adapted for providing a homogenous mixing flow under turbulent conditions to promote a thorough mixing of the first and second injection fluids to produce a substantially homogeneous mixed solution. Additionally, the mixing chamber 212j is also adapted to eliminate zones of stagnant fluid flow. The housing 202j is desirably formed from a medical-grade plastic material having sufficient rigidity to prevent any substantial expansion of the housing 202j during the injection procedure. For example, the housing 202j is adapted to retain its shape without appreciable expansion at an injection pressure of 1200 psi.

With specific reference to FIG. 22, the housing 202j includes a first portion 214j and a second portion 216j joined together at a seam 217j extending around the outer perimeter of the lateral sides of the first and second portions 214j, 216j. The seam 217j defines a seal between the first and second portions 214j, 216j to prevent fluid leakage from the mixing device 200j. The seam 217j includes a groove 219j provided on one of the first or second portions 214j, 216j of the housing 202j, and a corresponding projection 221j on the other of the first or second portions 214j, 216j such that the projection 221j is received inside the groove 219j. The first portion 214j and the second portion 216j are joined at the seam 217j by, for example, ultrasonic welding, UV bonding, or other joining techniques.

The housing 202j includes a first fluid port 206j for receiving a first injection fluid through a first fluid conduit (not shown) and a second fluid port 208*j* for receiving a second injection fluid through a second fluid conduit (not shown). First and second fluid ports 206*j*, 208*j* extend through the first and second portions 214*j*, 216*j* of the housing 202*j* and are in fluid communication with the mixing chamber 212*j* through first and second fluid orifices 226*j*, 228*j*, respectively. First and second fluid ports 206*j*, 208*j* are substantially parallel to each other. In other embodiments, first and second fluid ports 206*j*, 208*j* may be angled relative to a longitudinal axis of flow mixing device 200*j* such that fluid flow of the first and second injection fluids converges or diverges relative to the longitudinal axis. In one exemplary embodiment, a contrast medium may be supplied through the first fluid port 206*j* and saline may be injected through the second fluid port 208*j*. Fluid flowing through the first and second fluid ports 206*j*, 208*j* passes through the first and second fluid orifices 226*j*, 228*j* having a reduced cross-section relative to the first and second fluid ports 206*j*, 208*j*. First and second fluid orifices 226*j*, 228*j* have equal diameters. In another embodiment, the diameter of the first fluid orifice 226*j* may be larger or smaller relative to the diameter of the second fluid orifice 228*j*. First and second injection fluids mix within the mixing chamber 212*j* to form a mixed solution. The mixed solution is discharged from the mixing chamber 212*j* through a third fluid orifice 230*j* provided at a distal end of the first portion 214*j* of the housing 202*j*. The third fluid orifice 230*j* is in fluid communication with the third fluid port 210*j* that discharges the mixed fluid from the mixing device 200*j* through a fluid conduit (not shown).

With continued reference to FIG. 22, mixing chamber 212*j* is defined by two sinusoidal fluid paths 213*j* extending through the longitudinal length of the mixing chamber 212*j*. Each sinusoidal fluid path 213*j* is substantially circular in cross section (FIG. 23). The sinusoidal fluid paths 213*j* intersect at a plurality of intersection points 215*j* spaced apart at regular intervals over the longitudinal length of the mixing chamber 212*j*. At each intersection point 215*j*, fluid flow is combined from the portion of the sinusoidal fluid paths 213*j* upstream of the intersection point 215*j* and divided prior to continuing downstream of the intersection point 215*j*. The repeated combining and dividing fluid flow promotes turbulent mixing inside the mixing chamber 212*j* to produce a thoroughly mixed solution of the first and second injection fluids.

With reference to FIGS. 24-26, a flow mixing device 200*k* is illustrated in accordance with an eleventh embodiment. Flow mixing device 200*k* includes a housing 202*k* having a proximal end 204*k* opposite a distal end 205*k*. The proximal end 204*k* of the housing 202*k* includes a first fluid port 206*k* and a second fluid port 208*k* (shown in FIG. 25) which are connected or connectable to a respective first fluid line 116 and second fluid line 118. First injection fluid, such as a contrast solution, is delivered to the first fluid port 206*k* through the first fluid line 116, while the second injection fluid, such as saline, is delivered to the second fluid port 208*k*. The proximal end 204*k* of the housing 202*k* may include a connector (not shown) for connecting the first and second fluid lines 116, 118 to the flow mixing device 200*k*. The distal end 205*k* of the housing 202*k* includes a third fluid port 210*k* which is connected or connectable to the third fluid line 120. As the first and second injection fluids are introduced into the housing 202*k* of the flow mixing device 200*k*, they mix to produce a mixed solution of the first and second injection fluid. This mixed solution flows through the housing 202*k* and exits the flow mixing device 200*k* through the third fluid port 210*a*. The distal end 205*k* of the housing 202*k* may include a connector (not shown) for connecting the flow mixing device 200*k* to the third fluid line 120 or to a catheter.

The housing 202*k* of the flow mixing device 200*k* defines a mixing chamber 212*k* (shown in FIG. 25) where first and second injection fluids mix to form a mixed solution. The mixing chamber 212*k* is adapted for providing a homogenous mixing flow under turbulent conditions to promote a thorough mixing of the first and second injection fluids to produce a substantially homogeneous mixed solution. Additionally, the mixing chamber 212*k* is also adapted to eliminate zones of stagnant fluid flow. The housing 202*k* is desirably formed from a medical-grade plastic material having sufficient rigidity to prevent any substantial expansion of the housing 202*k* during the injection procedure. For example, the housing 202*k* is adapted to retain its shape without appreciable expansion at an injection pressure of 1200 psi.

With reference to FIGS. 25-26, the housing 202*k* includes a first portion 214*k* and a second portion 216*k* joined together at a seam 217*k* extending around the outer perimeter of the lateral sides of the first and second portions 214*k*, 216*k*. The seam 217*k* defines a seal between the first and second portions 214*k*, 216*k* to prevent fluid leakage from the mixing device 200*k*. The seam 217*k* includes a groove 219*k* provided on one of the first or second portions 214*k*, 216*k* of the housing 202*k*, and a corresponding projection 221*k* on the other of the first or second portions 214*k*, 216*k* such that the projection 221*k* is received inside the groove 219*k*.

The housing 202*k* includes a first fluid port 206*k* for receiving a first injection fluid through a first fluid conduit (not shown) and a second fluid port 208*k* for receiving a second injection fluid through a second fluid conduit (not shown). First and second fluid ports 206*k*, 208*k* extend through the first and second portion 214*k*, 216*k* of the housing 202*k* and are in fluid communication with the mixing chamber 212*k* through first and second fluid orifices 226*k*, 228*k*, respectively. First and second fluid ports 206*k*, 208*k* are substantially parallel to each other. In other embodiments, first and second fluid ports 206*k*, 208*k* may be angled relative a longitudinal axis of flow mixing device 200*k* such that fluid flow of the first and second injection fluids converges or diverges relative to the longitudinal axis. In one exemplary embodiment, a contrast medium may be supplied through the first fluid port 206*k* and saline may be injected through the second fluid port 208*k*. Fluid flowing through the first and second fluid ports 206*k*, 208*k* passes through the first and second fluid orifice 226*k*, 228*k* having a reduced cross-section relative to the first and second fluid ports 206*k*, 208*k*. First and second fluid orifices 226*k*, 228*k* have equal diameters. In another embodiment, the diameter of the first fluid orifice 226*k* may be larger or smaller relative to the diameter of the second fluid orifice 228*k*. First and second injection fluids mix within the mixing chamber 212*k* to form a mixed solution. The mixed solution is discharged from the mixing chamber 212*k* through a third fluid orifice 230*k* provided at a distal end of the first portion 214*k* of the housing 202*k*. The third fluid orifice 230*k* is in fluid communication with a third fluid port 210*k* that discharges the mixed fluid from the mixing device 200*k* through a fluid conduit (not shown).

The mixing chamber 212*k* is defined within the interior of the first portion 214*k*. The mixing chamber 212*k* has a generally cylindrical shape having a substantially circular cross-section. Alternatively, the cross-sectional shape of the mixing chamber 212*k* may be an ellipse or any other shape formed from a curved line. The mixing chamber 212*k* may have a first portion that narrows from the proximal end 218k to the distal end 220k to define a conical profile.

With continued reference to FIGS. 25-26, first and second fluid orifices 226k, 228k are in fluid communication with the mixing chamber 212k through first and second arcuate tubes 233k, 235k. The first and second arcuate tubes 233k, 235k are curved radially inward toward a longitudinal axis of the mixing chamber 212k such that they intersect at a juncture at the proximal end of the mixing chamber 212k. Due to the characteristics of the Coanda effect, a fluid jet of first or second injection fluid passing through the first and second arcuate tubes 233k, 235k will be attracted to the nearest surface, i.e., the surface closest to the longitudinal axis of the mixing chamber 212k. Once the fluid jet of the first injection fluid passes through the first arcuate tube 233k, the fluid jet will continue to flow in an arcuate manner within the mixing chamber 212k until it collides with an inner sidewall of the mixing chamber 212k, after which the fluid jet will be deflected in an opposite direction, thereby defining a sinusoidal travel path. Similarly, once the fluid jet of the second injection fluid passes through the second arcuate tube 235k, the fluid jet will continue to flow in an arcuate manner within the mixing chamber 212k until it collides with an inner sidewall of the mixing chamber 212k, after which the fluid jet will be deflected in an opposite direction, thereby defining a sinusoidal travel path opposite to the travel path of the first injection fluid. When the first fluid jet intersects with the second fluid jet, turbulent mixing of the first and second injection fluid occurs due to the difference in a radial velocity component of each fluid jet.

With reference to FIG. 27-28B, a flow mixing device 200l is illustrated in accordance with an eleventh embodiment. Flow mixing device 200l includes a housing 202l having a proximal end 204l opposite a distal end 205l. The proximal end 204l of the housing 202l may include a connector (not shown) for connecting the first and second fluid lines 116, 118 to the flow mixing device 200l. The distal end 205l of the housing 202l includes a third fluid port 210l which is connected or connectable to the third fluid line 120. As the first and second injection fluids are introduced into the housing 202l of the flow mixing device 200l, they mix to produce a mixed solution of the first and second injection fluids. This mixed solution flows through the housing 202l and exits the flow mixing device 200l through the third fluid port 210l. The distal end 205l of the housing 202l may include a connector (not shown) for connecting the flow mixing device 200l to the third fluid line 120 or to a catheter.

The housing 202l of the flow mixing device 200l defines a mixing chamber 212l (shown in FIG. 28A) where first and second injection fluids mix to form a mixed solution. The mixing chamber 212l is adapted for providing a homogenous mixing flow under turbulent conditions to promote a thorough mixing of the first and second injection fluids to produce a substantially homogeneous mixed solution. Additionally, the mixing chamber 212l is also adapted to eliminate zones of stagnant fluid flow. The housing 202l is desirably formed from a medical-grade plastic material having sufficient rigidity to prevent any substantial expansion of the housing 202l during the injection procedure. For example, the housing 202l is adapted to retain its shape without appreciable expansion at an injection pressure of 1200 psi.

As best shown in FIG. 28A, the mixing chamber 212l includes a plurality of grooves 2131 around the inner circumference of the mixing chamber 212l. The grooves 2131 extend helically through the longitudinal length of the mixing chamber 212l to define a "gun barrel rifling" shape.

As first and second injection fluids are delivered to the mixing chamber 212l, the grooves 2131 promote a swirling flow of the fluids along the longitudinal length of the mixing chamber 212l.

Figure 29:
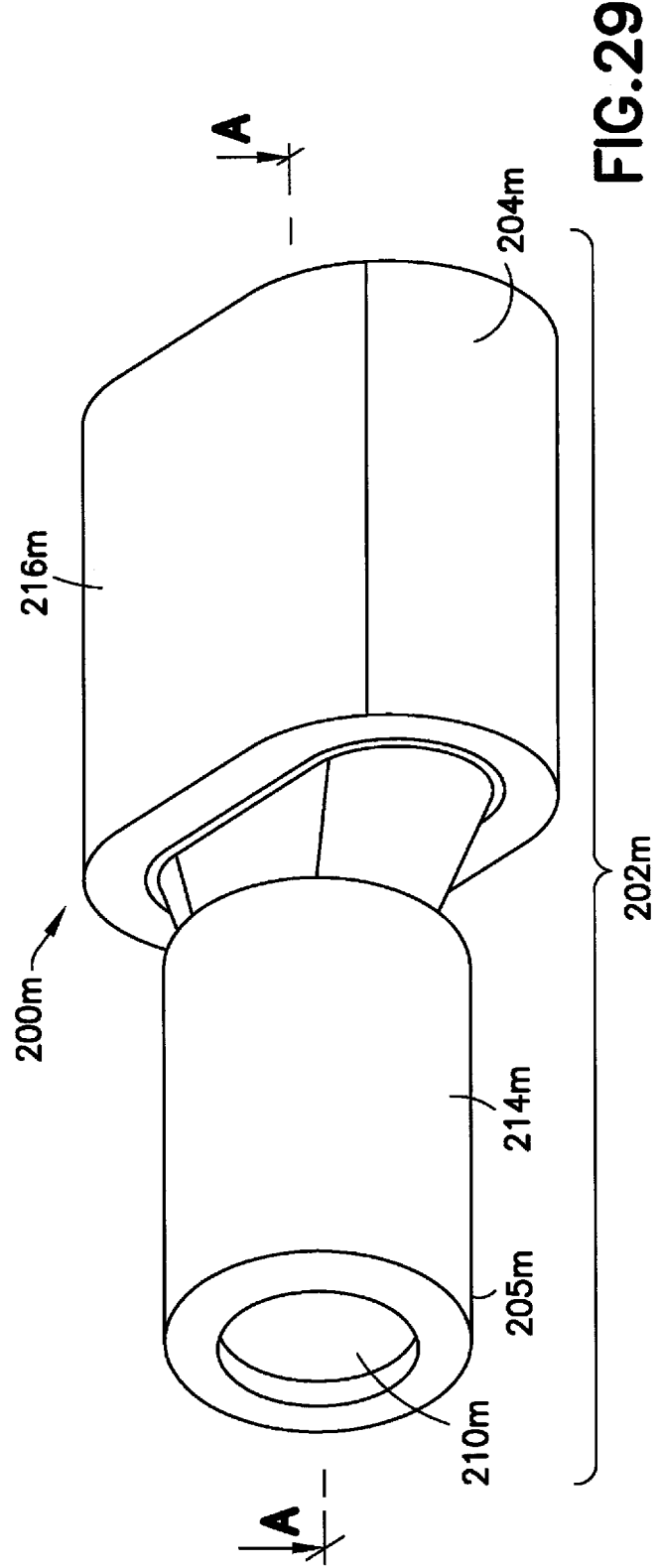
FIG. 29 is a top perspective view of a flow mixing device in accordance with a thirteenth embodiment.
Figure 30:
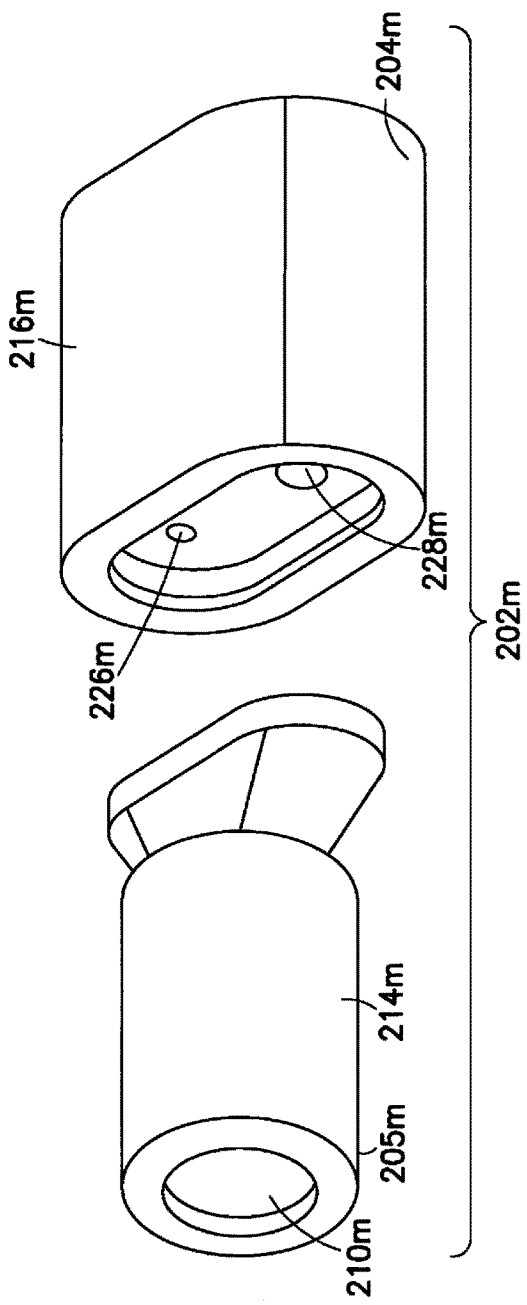
FIG. 30 is an exploded perspective view of the flow mixing device shown in FIG. 29.

With reference to FIGS. 29-30, a flow mixing device 200m is illustrated in accordance with a thirteenth embodiment. Flow mixing device 200m includes a housing 202m having a proximal end 204m opposite a distal end 205m. The proximal end 204m of the housing 202m includes a first fluid port 206m and a second fluid port 208m (shown in FIG. 31) which are connected or connectable to respective first fluid line 116 and second fluid line 118. First and second fluid ports 206m, 208m are substantially parallel to each other. In other embodiments, first and second fluid ports 206m, 208m may be angled relative to a longitudinal axis of flow mixing device 200m such that fluid flow of the first and second injection fluids converges or diverges relative to the longitudinal axis. The proximal end 204m of the housing 202m may include a connector (not shown) for connecting the first and second fluid lines 116, 118 to the flow mixing device 200m. The distal end 205m of the housing 202m includes a third fluid port 210m which is connected or connectable to the third fluid line 120. The distal end 205m of the housing 202m may include a connector (not shown) for connecting the flow mixing device 200m to the third fluid line 120 or to a catheter.

The housing 202m of the flow mixing device 200m defines a mixing chamber 212m (shown in FIG. 31) where first and second injection fluids mix to form a mixed solution. The mixing chamber 212m is adapted for providing a homogenous mixing flow under turbulent conditions to promote a thorough mixing of the first and second injection fluids to produce a substantially homogeneous mixed solution. Additionally, the mixing chamber 212m is also adapted to eliminate zones of stagnant fluid flow. The housing 202m is desirably formed from a medical-grade plastic material having sufficient rigidity to prevent any substantial expansion of the housing 202m during the injection procedure. For example, the housing 202m is adapted to retain its shape without appreciable expansion at an injection pressure of 1200 psi.

Figure 31:
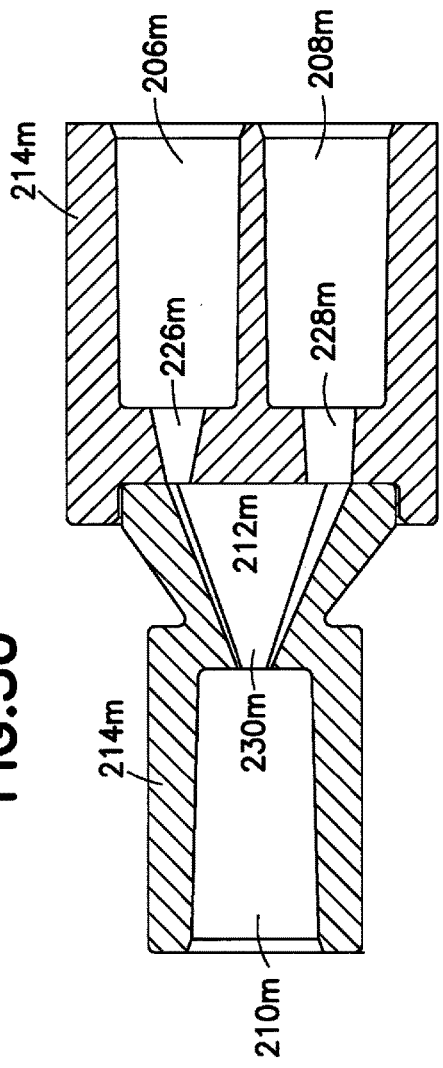
FIG. 31 is a cross-sectional view of the flow mixing device taken along line A-A shown in FIG. 29.

With reference to FIG. 31, fluid flowing through the first and second fluid ports 206m, 208m passes through the first and second fluid orifice 226m, 228m having a reduced cross-section relative to the first and second fluid ports 206m, 208m. The diameter of the first fluid orifice 226m is smaller relative to the diameter of the second fluid orifice 228m. During fluid injection, a first injection fluid, such as saline, is passed through the first fluid orifice 226m. Due to a reduced diameter of the first fluid orifice 226m relative to the second fluid orifice 228m, the first injection fluid experiences a higher pressure drop across the first fluid orifice 226m. The higher relative pressure drop is also associated with a change in the Reynolds number associated with the first injection fluid flowing through the first fluid orifice 226m and a corresponding transition from laminar to turbulent flow. For example, fluid flow of the first injection fluid prior to entering the first fluid orifice 226m is associated with a Reynolds number lower than 2300 (i.e., laminar flow). After experiencing the pressure drop caused by the diameter reduction between the first fluid port 206m and the first fluid orifice 226m, the Reynolds number of the first injection fluid will be higher than 4000 (i.e. turbulent flow). Similarly, fluid flow of the second injection fluid prior to entering the second fluid orifice 228m is also associated with a Reynolds number lower than 2300 (i.e., laminar flow); however, because the second injection fluid is not subjected to a high pressure drop due to the diameter reduction between the second fluid port 208m and the second fluid orifice 228m, the second injection fluid will maintain a laminar flow after passing through the second fluid orifice 228m. An additional benefit of reducing the diameter of the first fluid orifice 226m relative to the second fluid orifice 228m offsets any backflow of the first injection fluid when injecting a ratio of fluids having more than 50% of the second injection fluid that is more viscous than the first injection fluid. By combining a turbulent flow of a first injection fluid and a laminar flow of a second injection fluid in the mixing chamber 212m, the mixing of the two fluids to form a mixed solution is improved. The mixed solution is discharged from the mixing chamber 212m through a third fluid orifice 230m provided at a distal end of the first portion 214m of the housing 202m. The third fluid orifice 230m is in fluid communication with the fluid port 210m that discharges the mixed fluid from the mixing device 200m through a fluid conduit (not shown).

While embodiments of a fluid path set with a flow mixing device and methods of operation thereof were provided in the foregoing description, those skilled in the art may make modifications and alterations to these embodiments without departing from the scope and spirit of the invention. For example, any of the embodiments of the fluid path set with a flow mixing device can be adapted to receive a third (or more) injection fluid that is introduced into the mixing chamber of the flow mixing device for mixing with one or both of first and second injection fluids. Accordingly, the foregoing description is intended to be illustrative rather than restrictive.

Having described the various embodiments of the flow mixing device, a method of backflow compensation will now be described. In a typical multi-fluid injection procedure, an injection fluid, such as a contrast solution, is delivered from a contrast solution source to the patient using a powered or manual injector. The injected contrast solution is delivered to a desired site in a patient's body through a catheter inserted into the patient's body, such as the patient's groin area. Once the contrast fluid is delivered to the desired site, that area is imaged using a conventional imaging technique, such as angiography imagining or scanning. The contrast solution becomes clearly visible against the background of the surrounding tissue. However, because the contrast solution often comprises toxic substances that may be harmful to the patient if delivered in a high dosage or a high concentration, it is desirable to reduce contrast dosing to the patient, while maintaining an effective contrast amount necessary for effective imaging. By supplementing the overall contrast solution delivery procedure with saline, additional hydration of the patient occurs automatically and allows the body to remove the toxicity of the contrast solution. In addition to improved patient comfort level and less toxicity, introduction of saline at clinically significant pressures and flow rates also allows higher flow rates to be achieved at lower pressure settings on the injector.

To enable effective simultaneous flow delivery of first and second injection fluids, such as contrast solution and saline, substantially equal pressure must be present in each delivery line. In a powered injection system described above, it is desirable to actuate the piston elements substantially simultaneously in simultaneous flow delivery applications to equalize the pressure in each line. If the injector is operated with differential pressure in each delivery line of the fluid path set, the fluid in the lower pressure line may be stopped or reversed until sufficient pressure is achieved in the lower pressure line to enable flow in a desired direction. This time delay could reduce the usefulness of the image quality. This phenomenon is particularly evident in situations where contrast is injected at a significantly higher ratio relative to saline, such as 80% contrast to 20% saline injection protocol. The flow reversal is exacerbated at high injection pressures. In small dosage injections at a high injection pressure, flow reversal effectively stops the delivery of saline such that 100% contrast solution is injected, rather than the desired 80% contrast to 20% saline ratio. Similar inaccuracies occur at various other injection protocols, including, but not limited to 20% contrast to 80% saline ratio.

The above-described situation of flow reversal during powered injections at high contrast-to-saline ratio occurs due to injection system capacitance. Total system capacitance represents the amount of suppressed fluid (i.e., backflow volume) that is captured in the swelling of the injector system components due to pressure. Total system capacitance is inherent to each fluid injection system and depends on a plurality of factors, including injector construction, mechanical properties of materials used to construct the syringe, piston, pressure jacket surrounding the syringe, fluid lines delivering the contrast and saline to a flow mixing device, etc. The amount of back or reverse flow increases when the relative speed difference between the two pistons is large, the simultaneous fluid flow is through a small restriction, the speed of the total fluid injection is large, and the viscosity of the fluid is high. The back or reverse flow can prevent different ratios of simultaneously delivered fluid from ever occurring in certain injections, which can be a detriment for all two-syringe type injector systems.

In general, capacitance is directly correlative to injection pressure and inversely correlative to volume of contrast and saline in the syringes. For example, in one embodiment, capacitance during an injection at 1200 psi with 150 ml of contrast and saline remaining in the syringes is around 10 ml. In another embodiment, the capacitance volume can be from about 5 ml to about 9 ml. With reference to the graph shown in FIG. 32, several lines labeled A, B, and C show an increase in system capacitance relative to an increase in injection pressure at different syringe volumes. Line A, which corresponds to both syringes containing contrast solution or saline at maximum capacity. Lines B and C show the increase in capacitance with an increase in injection pressure for syringes having ⅔ and ⅓ of maximum fill volume, respectively.

Figure 33:
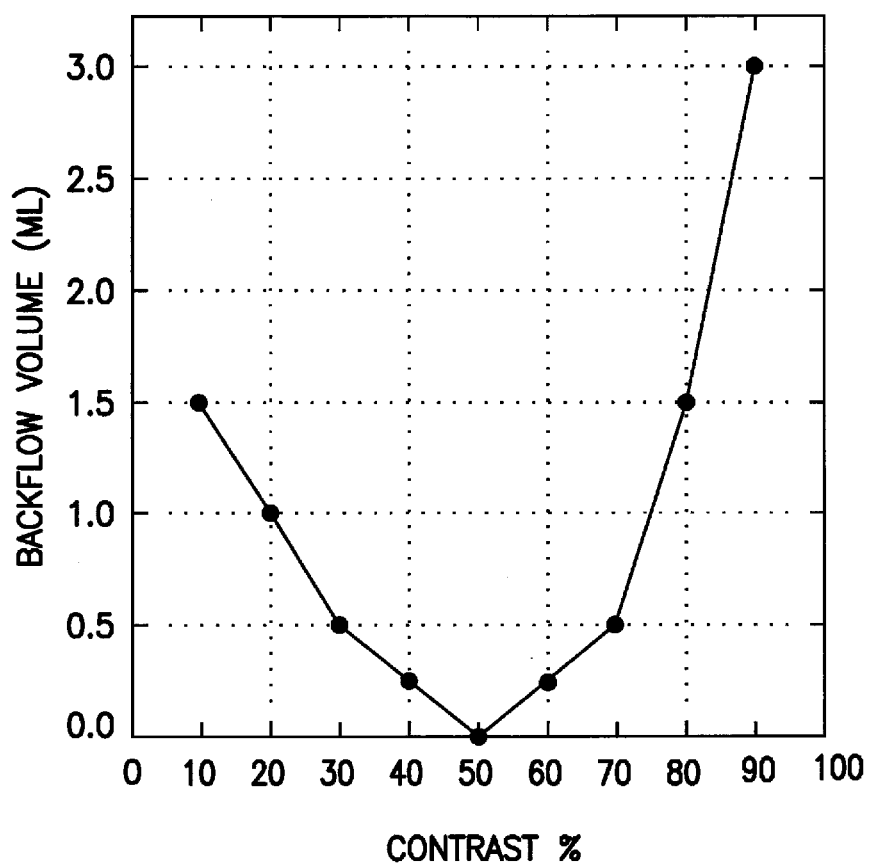
FIG. 33 is a graph of backflow volume relative to injection ratios of a first injection fluid and a second injection fluid.

Capacitance is also a function of the ratio at which the first and second injection fluids, such as contrast solution and saline, are injected. With reference to FIG. 33, an illustration of the relative change in backflow volume relative to the change in ratio between the contrast solution and saline is illustrated. At a 50%-50% ratio, where contrast solution and saline are injected in equal amounts, backflow volume is minimized because the capacitance on the contrast solution side is equal to the capacitance on the saline side of the injection system such that substantially equal pressures are present in each delivery line. Backflow may occur in situations where first and second injection fluids are delivered through long fluid conduits. However, as the injection ratio of contrast solution and saline changes, backflow volume increases corresponding to the increase in the ratio. As shown in FIG. 33, backflow volume is lower for low ratios of contrast solution and saline (i.e., higher saline concentration) than for high ratios (i.e., higher contrast concentration) due to the contrast solution having a significantly higher viscosity relative to saline.

Figure 34:
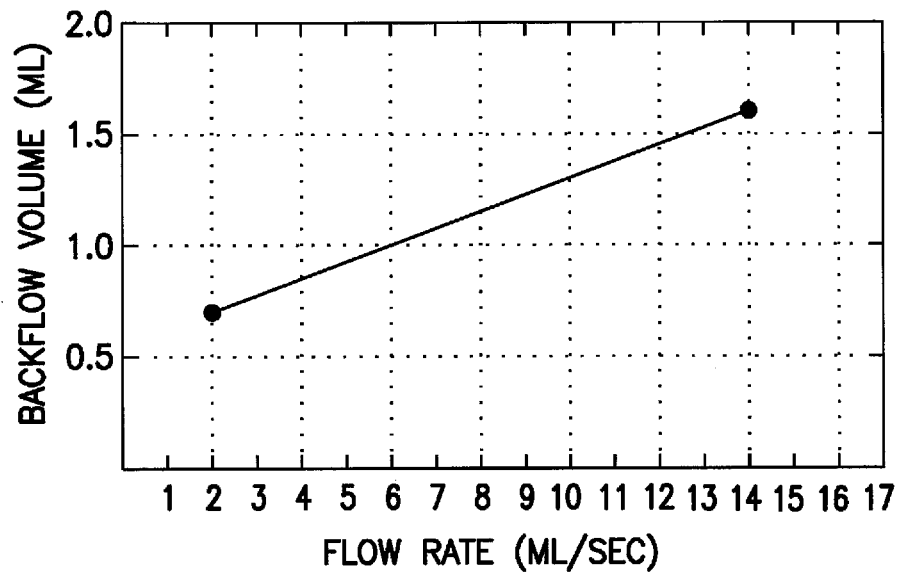
FIG. 34 is a graph of backflow volume relative to injection pressure for a single injection profile.
Figure 35:
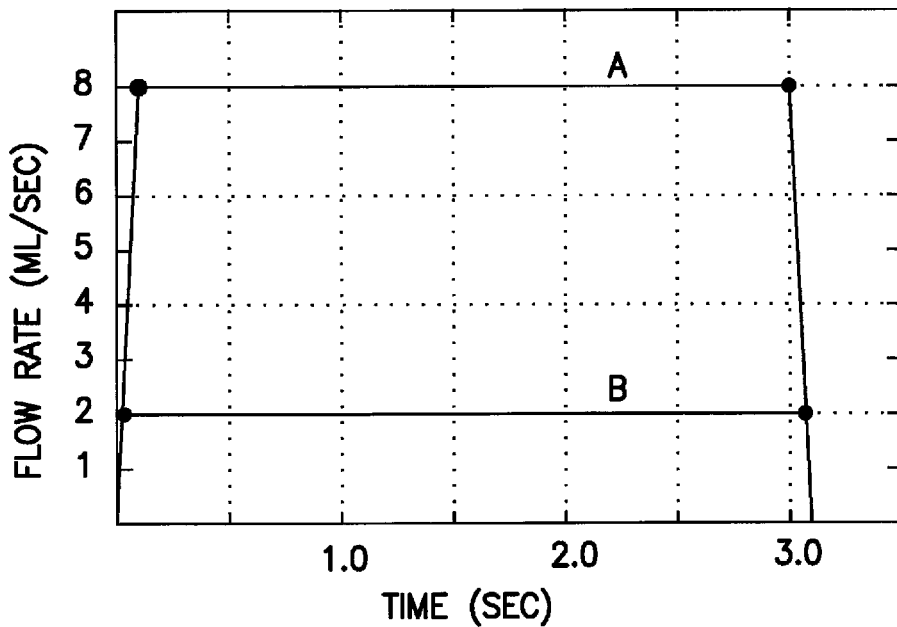
FIG. 35 is a velocity graph of pistons driving first and second injection fluids during an injection procedure.

With reference to FIG. 34, backflow volume is shown as a function of injection pressure for an injection protocol having a ratio of 80% contrast solution to 20% saline. Based on the injection pressure, desired fluid ratio cannot be realized at low injection volumes, where 100% of the injected fluid will be contrast solution. Even when the saline syringe is pressurized to a level to overcome the system capacitance, the overall fluid ratio is higher than the desired ratio. Typically, the desired ratio is selected by simultaneously activating the pistons and controlling the velocity and injection time to dispense the desired quantity of contrast solution and saline. FIG. 35 illustrates a velocity profile of pistons driving the first and second injection fluids (contrast solution and saline) for an 80%-20% injection protocol. As seen from the figure, velocity for each piston is kept constant during the injection duration, with the velocity of the piston injecting the contrast solution (labeled A) being four times faster than the velocity of the piston injecting the saline (labeled B). The acceleration of each piston from rest to a steady state velocity is identical.

A solution to the problem of eliminating backflow to compensate for system capacitance in a high contrast-to-saline ratio is to control the relative acceleration of the pistons in proportion to the capacitive swelling that is occurring. Thus, the ratio of simultaneous fluid delivery can be maintained. The difference in acceleration between the piston controlling the injection of the contrast solution and the piston controlling the injection of saline is determined by the predicted capacitance volume of the syringe with the correction factor dominated primarily by pressure and the axial position of the syringe plunger within the syringe barrel.

Figure 36:
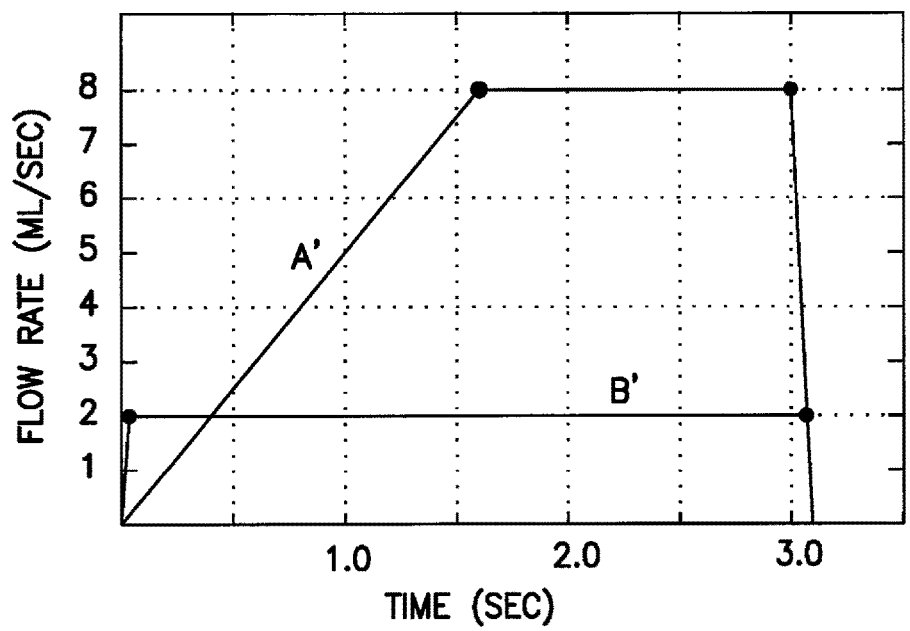
FIG. 36 is a modified velocity graph of pistons driving first and second injection fluids during an injection procedure.
Figure 37:
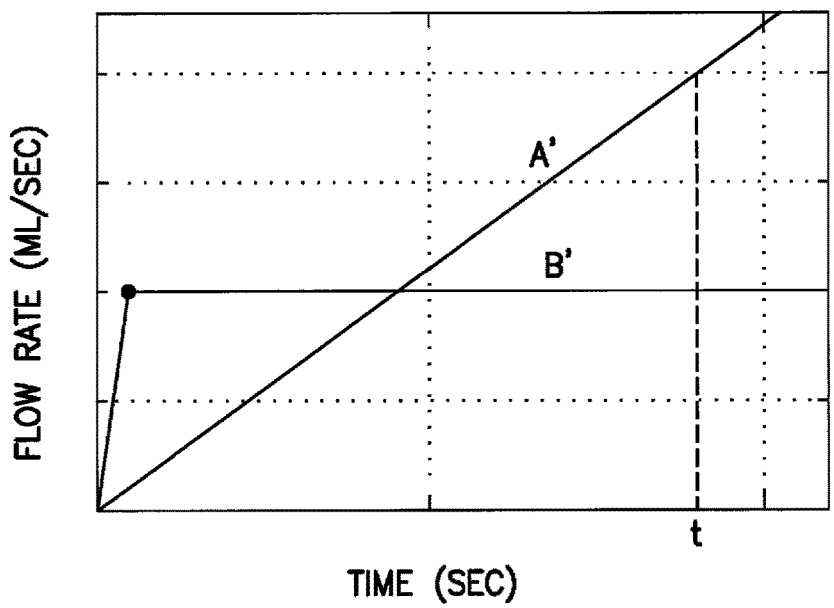
FIG. 37 is an enlarged portion of the graph shown in FIG. 36.

With reference to FIGS. 36-37, a velocity profile of pistons driving the first and second injection fluids (contrast solution and saline) for an 80%-20% injection protocol is shown where the acceleration of the piston driving the first injection fluid (contrast solution) from rest to a steady velocity is lower than the acceleration of the piston driving the second injection fluid (saline). Desirably, acceleration of the piston driving the second injection fluid is maximized such that the piston reaches its desired velocity in a least amount of time. The acceleration of the piston driving the first injection fluid is controlled as a function of relative velocities between the two pistons, the acceleration of the piston driving the second injection fluid, and a correction factor selected to compensate for the system capacitance. The acceleration of the piston driving the first injection fluid may be controlled only during the start of the injection procedure, or during the start and end of the injection procedure. The correction factor can be derived from empirical testing or derived from material and shape calculations of the fluid delivery set and the fluid injection system.

With reference to FIG. 37, a velocity profile of the two pistons controlling the injection of first and second injection fluids (i.e., contrast solution and saline, respectively) is shown in the initial stage of injection prior to the time when the piston driving the first injection fluid reaches steady state velocity (labeled A'). The velocity profile of the piston driving the second injection fluid is labeled as B'. Injection pressure at fluid paths of first and second injection fluids leading from the syringes are equalized when the areas under the velocity profiles A' and B' are substantially equal. The area under the curve for velocity profile A' can be calculated by the following equation: $U_1 = \frac{1}{2} V_1 * t$, where $V_1$ is the velocity of the piston driving the first injection fluid and t is time. The area under the curve for velocity profile B' can be calculated by the following equation: $U_2 = V_2 * t$, where $V_2$ is the velocity of the piston driving the second injection fluid and t is time. The calculation of $U_2$ does not account for any velocity gradient from the start of the injection procedure until a steady state velocity is achieved because acceleration of the piston driving the second injection fluid is maximized such that the initial slope of velocity profile B' is essentially vertical. Based on the above equations, the areas under the velocity profiles A' and B' are substantially equal at a time when the velocity of the piston driving the first injection fluid is equal to twice the velocity of the piston driving the second injection fluid (i.e., $V_1 = 2 * V_2$). Because the acceleration of the piston driving the second injection fluid is known (i.e., the maximum acceleration $A_2$ that the piston can achieve), the acceleration of the piston driving the first injection fluid can be calculated as a function of the velocity ratio between the two pistons. The following equation governs the acceleration value $A_1$ of the piston driving the first injection fluid: $A_1 = A_2 / (c * (V_1 / V_2))$, where c is a scalar correction factor selected to compensate for the system capacitance and minimize the backflow volume. As noted above, the correction factor c can be derived from empirical testing based on a plurality of different injection pressures and fill volumes of the syringes containing the first and second injection fluids. Alternatively, the correction factor c can be derived from material and shape calculations of the fluid delivery set and the fluid injection system. The correction factor controls the acceleration $A_1$ of the piston driving the first injection fluid in the initial stage of fluid injection in order to compensate for the system capacitance at a given injection pressure and the fill volume of the syringes containing the first and second injection fluids. The difference in acceleration between the piston controlling the injection of the contrast solution and the piston controlling the injection of saline is determined by the predicted capacitance volume of the syringes with the correction factor c dominated primarily by pressure and the fill volume of the syringe.

Figure 38:
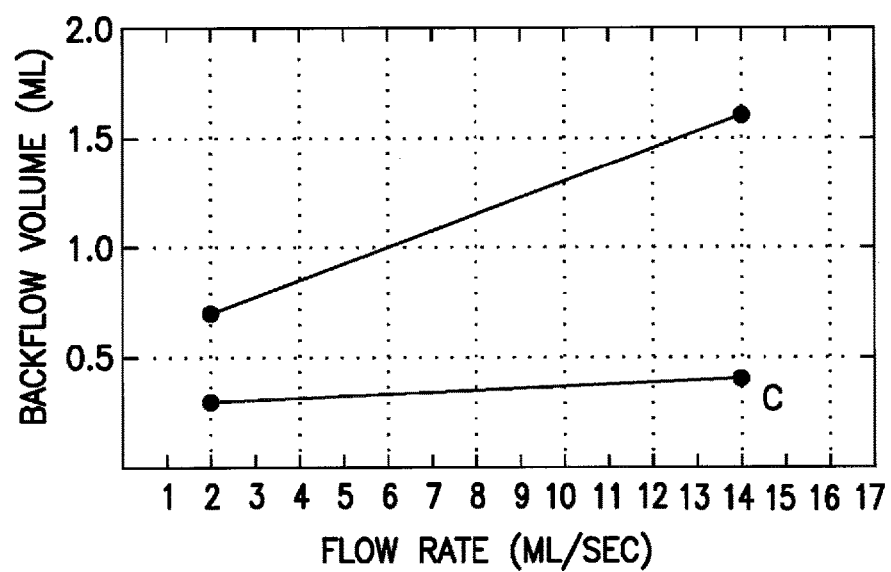
FIG. 38 is a graph of backflow volume relative to injection pressure for a plurality of injection profiles.

As shown in FIG. 38, a plurality of backflow volume curves are shown as a function of injection pressure for uncorrected acceleration value for the piston driving the first injection fluid and a corrected value for correction factors c. The correction factor is chosen to minimize or eliminate the backflow volume across all injection pressures for a given fill volume of the syringes containing the first and second injection fluids. Minimizing or eliminating the backflow volume ensures that the actual ratio of the first and second injection fluids is maintained at all stages of the injection process.

While several embodiments were provided in the foregoing description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A flow mixing device configured for use within a fluid path between a fluid injector and a fluid line connected to a patient, the flow mixing device comprising:
   a housing having a proximal end opposite a distal end spaced apart along a longitudinal axis, the housing comprising a first portion and a second portion joined together at a seam extending in a direction along the longitudinal axis around an outer perimeter of lateral sides of the first portion and the second portion;

a first fluid port for receiving a first injection fluid and a second fluid port for receiving a second injection fluid;

a mixing chamber disposed within the housing between the proximal and distal ends of the housing, the mixing chamber being in fluid communication with the first and second fluid ports for mixing the first and second injection fluids;

a third fluid port at the distal end of the housing and in fluid communication with the mixing chamber for discharging a mixture of the first and second injection fluids; and a turbulent flow inducing member disposed within the mixing chamber for promoting turbulent mixing of the first and second injection fluids, wherein the seam comprises a groove provided on one of the first portion and the second portion of the housing and a corresponding projection on the other of the first portion and the second portion of the housing such that the projection is received within the groove.

2. The flow mixing device of claim 1, wherein the seam defines a seal between the first portion and the second portion of the housing to prevent fluid leakage from the mixing chamber.

3. The flow mixing device of claim 1, wherein the mixing chamber is adapted to eliminate zones of stagnant fluid flow.

4. The flow mixing device of claim 1, wherein the housing retains its shape without appreciable expansion at an injection pressure of 1200 psi.

5. The flow mixing device of claim 1, wherein the first fluid port and the second fluid port are angled relative to the longitudinal axis of the flow mixing device so a fluid flow of the first injection fluid and the second injection fluid converges or diverges relative to the longitudinal axis.

6. The flow mixing device of claim 1, wherein the turbulent flow inducing member comprises two sinusoidal fluid paths extending through the mixing chamber, and wherein the two sinusoidal fluid paths intersect at a plurality of intersection points within the mixing chamber.

7. The flow mixing device of claim 6, wherein, at each of the plurality of intersection points, fluid flow is combined from upstream portions of the two sinusoidal fluid paths and divided prior to continuing downstream of each of the intersection points.

8. The flow mixing device of claim 6, wherein the plurality of intersection points are spaced apart at regular intervals over a longitudinal length of the mixing chamber.

9. The flow mixing device of claim 1, wherein the turbulent flow inducing member comprises a first arcuate tube in fluid communication with the first fluid port and a second arcuate tube in fluid communication with the second fluid port, wherein the first arcuate tube and second arcuate tube are curved radially inward toward a central axis of the mixing chamber.

10. The flow mixing device of claim 9, wherein the mixing chamber has a cross-section that is circular, elliptical, or shaped to define a curved cross-section.

11. The flow mixing device of claim 9, wherein the mixing chamber has an interior portion that narrows from the proximal end to the distal end of the housing to define a conical profile.

12. The flow mixing device of claim 9, wherein fluid mixing at a juncture between the first and second arcuate tubes is influenced by a Coanda effect caused by the first injection fluid and the second injection fluid flowing through the first arcuate tube and the second arcuate tube.

13. A fluid path set comprising:
a first fluid line having a proximal end and a distal end, the proximal end fluidly connectable to a source of a first injection fluid;

a second fluid line having a proximal end and a distal end, the proximal end fluidly connectable to a source of a second injection fluid;

a flow mixing device in fluid communication with the distal ends of the first and second fluid lines at a proximal end of the flow mixing device, the flow mixing device comprising:

a housing having a proximal end opposite a distal end spaced apart along a longitudinal axis, the housing comprising a first portion and a second portion joined together at a seam extending in a direction along the longitudinal axis around an outer perimeter of lateral sides of the first portion and the second portion;

a first fluid port provided at the proximal end of the housing for receiving the first injection fluid and a second fluid port provided at the proximal end of the housing for receiving the second injection fluid;

a mixing chamber disposed within the housing between the proximal and distal ends, the mixing chamber being in fluid communication with the first and second fluid ports for mixing the first and second injection fluids;

a third fluid port provided at the distal end of the housing and in fluid communication with the mixing chamber for discharging a mixture of the first and second injection fluids; and a turbulent flow inducing member disposed within the mixing chamber for promoting turbulent mixing of the first and second injection fluids; and a third fluid line in fluid communication with the flow mixing device at a distal end of the flow mixing device, wherein the seam comprises a groove provided on one of the first portion and the second portion of the housing and a corresponding projection on the other of the first portion and the second portion of the housing such that the projection is received within the groove.

14. The fluid path set of claim 13, wherein the seam defines a seal between the first portion and the second portion of the housing to prevent fluid leakage from the mixing chamber.

15. The fluid path set of claim 13, wherein the turbulent flow inducing member comprises two sinusoidal fluid paths extending through the mixing chamber, and wherein the two sinusoidal fluid paths intersect at a plurality of intersection points within the mixing chamber.

16. The fluid path set of claim 13, wherein the turbulent flow inducing member comprises a first arcuate tube in fluid communication with the first fluid port and a second arcuate tube in fluid communication with the second fluid port, wherein the first arcuate tube and the second arcuate tube are curved radially inward toward a central axis of the mixing chamber and fluid mixing at a juncture between the first and second arcuate tubes is influenced by a Coanda effect caused by the first injection fluid and the second injection fluid flowing through the first arcuate tube and the second arcuate tube.

17. A flow mixing device configured for use within a fluid path between a fluid injector and a fluid line connected to a patient, the flow mixing device comprising:
a housing having a proximal end opposite a distal end spaced apart along a longitudinal axis, the housing comprising a first portion and a second portion joined together at a seam extending in a direction along the longitudinal axis around an outer perimeter of lateral sides of the first portion and the second portion;

a first fluid port provided at the proximal end of the housing for receiving a first injection fluid and a second fluid port provided at the proximal end of the housing for receiving a second injection fluid;

a mixing chamber disposed within the housing between the proximal and distal ends, the mixing chamber being in fluid communication with the first and second fluid ports for mixing the first and second injection fluids;

a third fluid port provided at the distal end of the housing and in fluid communication with the mixing chamber for discharging a mixture of the first and second injection fluids; and a turbulent flow inducing member disposed within the mixing chamber for promoting turbulent mixing of the first and second injection fluids, wherein the seam defines a seal between the first portion and the second portion of the housing to prevent fluid leakage from the mixing chamber, wherein the seam comprises a groove provided on one of the first portion and the second portion of the housing and a corresponding projection on the other of the first portion and the second portion of the housing such that the projection is received within the groove to provide the seal, wherein the turbulent flow inducing member comprises two sinusoidal fluid paths extending through the mixing chamber, and wherein the two sinusoidal fluid paths intersect at a plurality of intersection points within the mixing chamber.

18. The fluid path set of claim 14, wherein the turbulent flow inducing member comprises two sinusoidal fluid paths extending through the mixing chamber, and wherein the two sinusoidal fluid paths intersect at a plurality of intersection points within the mixing chamber.

* * * * *

UNITED STATES PATENT AND TRADEMARK OFFICE
CERTIFICATE OF CORRECTION

PATENT NO.        : 10,029,220 B2
APPLICATION NO.   : 15/417945
DATED             : July 24, 2018
INVENTOR(S)       : Schriver et al.

Page 1 of 1

It is certified that error appears in the above-identified patent and that said Letters Patent is hereby corrected as shown below:

On the Title Page
In Item (72), under "Inventors", in Column 1, Line 8, delete "Harrison City," and insert -- Trafford, --, therefor.

Figure 32:
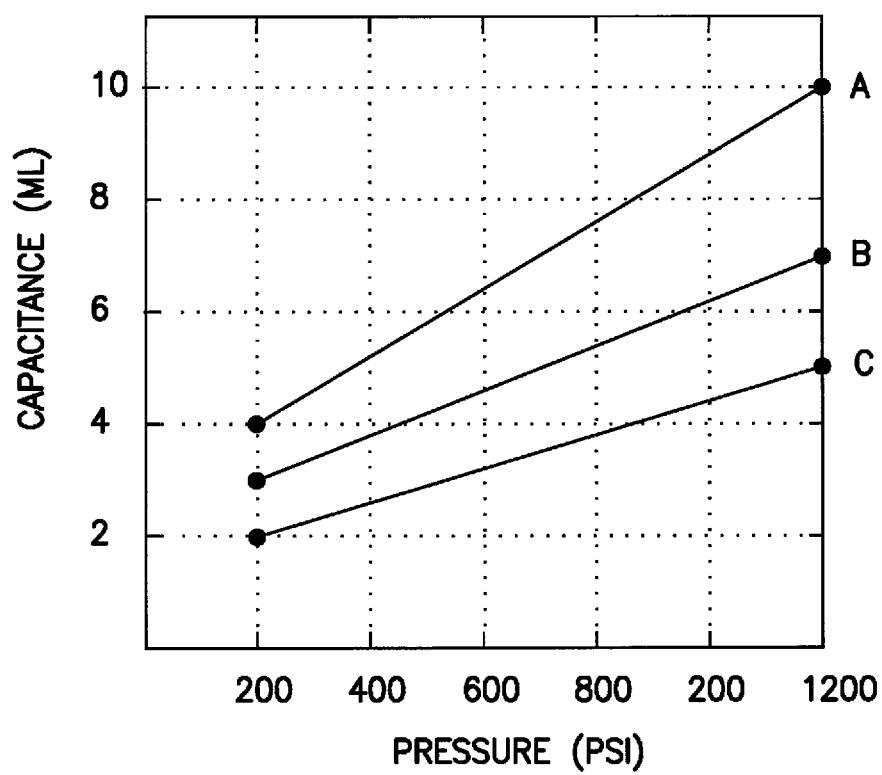
FIG. 32 is a graph of capacitance volume relative to injection pressure for a plurality of fill volumes of first and second injection fluids.

In the Drawings
In Fig. 7, Sheet 7 of 34, delete main designator "206b" and insert main designator -- 200b --, therefor.
In Fig. 32, Sheet 30 of 34, delete "800 200" and insert -- 800 1000 --, therefor.

In the Specification
In Column 20, Lines 53-54, delete "247h, 246h'" and insert -- 247h, 247h' --, therefor.

Signed and Sealed this
Thirtieth Day of October, 2018

Andrei Iancu
*Director of the United States Patent and Trademark Office*